(12) United States Patent
Croteau et al.

(10) Patent No.: US 6,303,330 B1
(45) Date of Patent: Oct. 16, 2001

(54) GERANYL DIPHOSPHATE SYNTHASE LARGE SUBUNIT, AND METHODS OF USE

(75) Inventors: Rodney B. Croteau, Pullman, WA (US); Charles C. Burke, Moscow, ID (US); Mark R. Wildung, Colfax, WA (US)

(73) Assignee: Washington State University Research Foundation, Pullma, WA (US)

( * ) Notice: Subject to any disclaimer, the term of this patent is extended or adjusted under 35 U.S.C. 154(b) by 0 days.

(21) Appl. No.: 09/420,211

(22) Filed: Oct. 18, 1999

Related U.S. Application Data

(63) Continuation-in-part of application No. PCT/US98/21772, filed on Oct. 15, 1998, which is a continuation-in-part of application No. 08/951,924, filed on Oct. 16, 1997, now Pat. No. 5,876,964.

(51) Int. Cl.[7] .................... C12N 15/63; C12N 15/29; C12N 5/10; C12N 1/21
(52) U.S. Cl. .................... 435/69; 435/325; 435/419; 435/252.3; 435/320.1; 536/23.6
(58) Field of Search .................... 435/69.1, 325, 435/419, 252.3, 320.1; 536/23.6

(56) References Cited

U.S. PATENT DOCUMENTS 5,876,964 * 3/1999 Croteau .................... 435/69.1

OTHER PUBLICATIONS

J. Gershenzon et al., *Anal. Biochem.*, 200:130–138, 1992.

* cited by examiner

*Primary Examiner*—John S. Brusca
(74) *Attorney, Agent, or Firm*—Christensen O'Connor Johnson Kindness PLLC

(57) ABSTRACT

A cDNA encoding geranyl diphosphate synthase large subunit from peppermint has been isolated and sequenced, and the corresponding amino acid sequence has been determined. Replicable recombinant cloning vehicles are provided which code for geranyl diphosphate synthase large subunit). In another aspect, modified host cells are provided that have been transformed, transfected, infected and/or injected with a recombinant cloning vehicle and/or DNA sequence encoding geranyl diphosphate synthase large subunit. In yet another aspect, the present invention provides isolated, recombinant geranyl diphosphate synthase protein comprising an isolated, recombinant geranyl diphosphate synthase large subunit protein and an isolated, recombinant geranyl diphosphate synthase small subunit protein. Thus, systems and methods are provided for the recombinant expression of geranyl diphosphate synthase.

24 Claims, 2 Drawing Sheets

SEQUENCE LISTING

```
<160> NUMBER OF SEQ ID NOS: 15

<210> SEQ ID NO 1
<211> LENGTH: 1131
<212> TYPE: DNA
<213> ORGANISM: Mentha piperita
<220> FEATURE:
<221> NAME/KEY: CDS
<222> LOCATION: (1)..(1131)

<400> SEQUENCE: 1 atg agt gct ctt gtt aat cct gtg gcg aaa tgg cct cag acg atc ggc      48
Met Ser Ala Leu Val Asn Pro Val Ala Lys Trp Pro Gln Thr Ile Gly
 1               5                  10                  15 gtt aaa gat gtt cac ggc ggc cgg agg cgg aga tcc aga tcc act ctc      96
Val Lys Asp Val His Gly Gly Arg Arg Arg Arg Ser Arg Ser Thr Leu
             20                  25                  30 ttt caa tcc cat cca ctt cgc act gaa atg cct ttc tct ctc tac ttc     144
Phe Gln Ser His Pro Leu Arg Thr Glu Met Pro Phe Ser Leu Tyr Phe
         35                  40                  45 tca tcc ccc ctc aaa gct ccc gcc act ttt tcc gtt tct gca gtt tat     192
Ser Ser Pro Leu Lys Ala Pro Ala Thr Phe Ser Val Ser Ala Val Tyr
 50                  55                  60 acc aaa gag ggc agc gaa att agg gat aaa gat ccg gcg cct tcg act     240
Thr Lys Glu Gly Ser Glu Ile Arg Asp Lys Asp Pro Ala Pro Ser Thr
 65                  70                  75                  80 tcg ccg gcg ttc gat ttc gac gga tac atg ctc cgg aag gcg aaa tcc     288
Ser Pro Ala Phe Asp Phe Asp Gly Tyr Met Leu Arg Lys Ala Lys Ser
                 85                  90                  95 gtc aac aag gcg ttg gaa gcg gcg gtg cag atg aag gag ccg ctg aag     336
Val Asn Lys Ala Leu Glu Ala Ala Val Gln Met Lys Glu Pro Leu Lys
            100                 105                 110 atc cac gag tcc atg cgg tac tcc ctt ctc gcc ggc ggc aag aga gtg     384
Ile His Glu Ser Met Arg Tyr Ser Leu Leu Ala Gly Gly Lys Arg Val
        115                 120                 125 cgt cct atg ctg tgc atc gcg gcc tgc gag ctc gtc ggc ggc gac gag     432
Arg Pro Met Leu Cys Ile Ala Ala Cys Glu Leu Val Gly Gly Asp Glu
    130                 135                 140 tcc acg gcg atg ccg gcg gcc tgc gcc gtc gag atg atc cac acg atg     480
Ser Thr Ala Met Pro Ala Ala Cys Ala Val Glu Met Ile His Thr Met
145                 150                 155                 160 tcg ctg atg cac gac gac ctc cca tgc atg gac aac gac gac ctc cgc     528
Ser Leu Met His Asp Asp Leu Pro Cys Met Asp Asn Asp Asp Leu Arg
                165                 170                 175 cgc ggc aag ccg acg aac cac atg gct ttc ggc gag agc gtg gcg gtc     576
Arg Gly Lys Pro Thr Asn His Met Ala Phe Gly Glu Ser Val Ala Val
            180                 185                 190 ctc gcc ggc gac gcc ctc ctc tcc ttc gcg ttc gag cac gtg gcg gcg     624
Leu Ala Gly Asp Ala Leu Leu Ser Phe Ala Phe Glu His Val Ala Ala
        195                 200                 205
```

-continued

| | |
|---|---|
| gcg acc aaa ggc gcg ccg ccg gag cgg atc gtg agg gtc ctc ggc gag<br>Ala Thr Lys Gly Ala Pro Pro Glu Arg Ile Val Arg Val Leu Gly Glu<br>    210                          215                          220 | 672 |
| ctg gct gtc tcg atc ggg tcg gag ggg ctg gtg gcg ggg cag gtg gtg<br>Leu Ala Val Ser Ile Gly Ser Glu Gly Leu Val Ala Gly Gln Val Val<br>225                          230                          235                        240 | 720 |
| gac gtc tgc tcg gag ggg atg gcg gag gtc ggg ctg gac cac ctc gag<br>Asp Val Cys Ser Glu Gly Met Ala Glu Val Gly Leu Asp His Leu Glu<br>                  245                          250                          255 | 768 |
| ttc atc cac cac cac aag acg gcg gcg ctg ctg cag ggg tcg gtg gtt<br>Phe Ile His His His Lys Thr Ala Ala Leu Leu Gln Gly Ser Val Val<br>    260                          265                          270 | 816 |
| ctg ggg gcg att ttg ggc ggc gga aag gag gag gag gtg gcg aag ctg<br>Leu Gly Ala Ile Leu Gly Gly Gly Lys Glu Glu Glu Val Ala Lys Leu<br>              275                        280                        285 | 864 |
| aga aaa ttc gcg aat tgc atc gga ttg ctg ttt cag gtg gtg gac gat<br>Arg Lys Phe Ala Asn Cys Ile Gly Leu Leu Phe Gln Val Val Asp Asp<br>290                          295                          300 | 912 |
| atc cta gat gtg acg aaa tcg tcc aag gaa ttg ggg aag acg gcg ggg<br>Ile Leu Asp Val Thr Lys Ser Ser Lys Glu Leu Gly Lys Thr Ala Gly<br>305                          310                          315                        320 | 960 |
| aag gat ctg gtg gcg gat aaa acc aca tat ccg aag cta ata ggc gtg<br>Lys Asp Leu Val Ala Asp Lys Thr Thr Tyr Pro Lys Leu Ile Gly Val<br>              325                        330                        335 | 1008 |
| gag aaa tcc aag gaa ttc gcg gat cgg ttg aac agg gag gcg cag gag<br>Glu Lys Ser Lys Glu Phe Ala Asp Arg Leu Asn Arg Glu Ala Gln Glu<br>                  340                        345                        350 | 1056 |
| cag ctc ctc cat ttt cat cct cat agg gca gct cca ttg att gct ctc<br>Gln Leu Leu His Phe His Pro His Arg Ala Ala Pro Leu Ile Ala Leu<br>              355                        360                        365 | 1104 |
| gcc aat tat att gct tat agg gac aat<br>Ala Asn Tyr Ile Ala Tyr Arg Asp Asn<br>370                        375 | 1131 |

<210> SEQ ID NO 2
<211> LENGTH: 377
<212> TYPE: PRT
<213> ORGANISM: Mentha piperita

<400> SEQUENCE: 2

Met Ser Ala Leu Val Asn Pro Val Ala Lys Trp Pro Gln Thr Ile Gly
  1                 5                  10                 15

Val Lys Asp Val His Gly Gly Arg Arg Arg Ser Arg Ser Thr Leu
              20                  25                  30

Phe Gln Ser His Pro Leu Arg Thr Glu Met Pro Phe Ser Leu Tyr Phe
           35                    40                  45

Ser Ser Pro Leu Lys Ala Pro Ala Thr Phe Ser Val Ser Ala Val Tyr
 50                  55                  60

Thr Lys Glu Gly Ser Glu Ile Arg Asp Lys Asp Pro Ala Pro Ser Thr
 65                  70                  75                  80

Ser Pro Ala Phe Asp Phe Asp Gly Tyr Met Leu Arg Lys Ala Lys Ser
                  85                  90                  95

Val Asn Lys Ala Leu Glu Ala Ala Val Gln Met Lys Glu Pro Leu Lys
          100                  105                 110

Ile His Glu Ser Met Arg Tyr Ser Leu Leu Ala Gly Gly Lys Arg Val
         115                  120                125

Arg Pro Met Leu Cys Ile Ala Ala Cys Glu Leu Val Gly Gly Asp Glu
    130                   135                  140

```
Ser Thr Ala Met Pro Ala Ala Cys Ala Val Glu Met Ile His Thr Met
145                 150                 155                 160

Ser Leu Met His Asp Asp Leu Pro Cys Met Asp Asn Asp Leu Arg
            165                 170                 175

Arg Gly Lys Pro Thr Asn His Met Ala Phe Gly Glu Ser Val Ala Val
            180                 185                 190

Leu Ala Gly Asp Ala Leu Leu Ser Phe Ala Phe Glu His Val Ala Ala
            195                 200                 205

Ala Thr Lys Gly Ala Pro Pro Glu Arg Ile Val Arg Val Leu Gly Glu
210                 215                 220

Leu Ala Val Ser Ile Gly Ser Glu Gly Leu Val Ala Gly Gln Val Val
225                 230                 235                 240

Asp Val Cys Ser Glu Gly Met Ala Glu Val Gly Leu Asp His Leu Glu
            245                 250                 255

Phe Ile His His His Lys Thr Ala Ala Leu Leu Gln Gly Ser Val Val
            260                 265                 270

Leu Gly Ala Ile Leu Gly Gly Gly Lys Glu Glu Glu Val Ala Lys Leu
            275                 280                 285

Arg Lys Phe Ala Asn Cys Ile Gly Leu Leu Phe Gln Val Val Asp Asp
            290                 295                 300

Ile Leu Asp Val Thr Lys Ser Ser Lys Glu Leu Gly Lys Thr Ala Gly
305                 310                 315                 320

Lys Asp Leu Val Ala Asp Lys Thr Thr Tyr Pro Lys Leu Ile Gly Val
                325                 330                 335

Glu Lys Ser Lys Glu Phe Ala Asp Arg Leu Asn Arg Glu Ala Gln Glu
            340                 345                 350

Gln Leu Leu His Phe His Pro His Arg Ala Ala Pro Leu Ile Ala Leu
            355                 360                 365

Ala Asn Tyr Ile Ala Tyr Arg Asp Asn
            370                 375

<210> SEQ ID NO 3
<211> LENGTH: 5
<212> TYPE: PRT
<213> ORGANISM: Mentha piperita

<400> SEQUENCE: 3

Leu Ile Gly Val Glu
1               5

<210> SEQ ID NO 4
<211> LENGTH: 5
<212> TYPE: PRT
<213> ORGANISM: Mentha piperita

<400> SEQUENCE: 4

Tyr Ile Ala Tyr Arg
1               5

<210> SEQ ID NO 5
<211> LENGTH: 15
<212> TYPE: PRT
<213> ORGANISM: Mentha piperita

<400> SEQUENCE: 5

Thr Ala Ala Leu Leu Thr Gly Ser Val Val Leu Gly Ala Ile Leu
1               5                   10                  15
```

```
<210> SEQ ID NO 6
<211> LENGTH: 9
<212> TYPE: PRT
<213> ORGANISM: Mentha piperita

<400> SEQUENCE: 6

Glu Ala Val Glu Thr Leu Leu His Phe
 1               5

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(26)
<223> OTHER INFORMATION: PCR primer GG23F

<400> SEQUENCE: 7
gaattgcatc ggattgctgt ttcagg                                      26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(24)
<223> OTHER INFORMATION: PCR primer GG23R

<400> SEQUENCE: 8
ccgccaccag atccttcccc gccg                                        24

<210> SEQ ID NO 9
<211> LENGTH: 101
<212> TYPE: DNA
<213> ORGANISM: Mentha piperita

<400> SEQUENCE: 9
cgaattgcat cggattgctg tttcaggtgg tggacgatat cctagatgtg acgaaatcgt    60
ccaaggaatt ggggaagacg gcggggaagg atctggtggc g                      101

<210> SEQ ID NO 10
<211> LENGTH: 1131
<212> TYPE: DNA
<213> ORGANISM: Mentha piperita
<220> FEATURE:
<221> NAME/KEY: CDS
<222> LOCATION: (6)..(944)

<400> SEQUENCE: 10 tcaaa atg gcc att aat ctc tcc cat atc aac tcc aaa aca tgt ttc cct    50
      Met Ala Ile Asn Leu Ser His Ile Asn Ser Lys Thr Cys Phe Pro
       1               5                  10                  15 ctc aaa aca aga tct gat ctc agc cgt tct tct tcc gcg cgt tgc atg     98
Leu Lys Thr Arg Ser Asp Leu Ser Arg Ser Ser Ser Ala Arg Cys Met
             20                  25                  30 cca act gcc gcc gct gcc gcc ttc ccc act atc gcc acc gcc gcc caa    146
Pro Thr Ala Ala Ala Ala Ala Phe Pro Thr Ile Ala Thr Ala Ala Gln
         35                  40                  45
```

-continued

| | |
|---|---|
| agt cag ccg tac tgg gcc gcc atc gag gcc gac ata gag aga tac ctg<br>Ser Gln Pro Tyr Trp Ala Ala Ile Glu Ala Asp Ile Glu Arg Tyr Leu<br>          50                     55                     60 | 194 |
| aag aaa tcc atc aca ata agg ccg ccg gag aca gtt ttc ggg ccc atg<br>Lys Lys Ser Ile Thr Ile Arg Pro Pro Glu Thr Val Phe Gly Pro Met<br>65                       70                     75 | 242 |
| cac cac ctc acc ttc gcc gcc cca gcc acc gcc gcc tcc acc cta tgc<br>His His Leu Thr Phe Ala Ala Pro Ala Thr Ala Ala Ser Thr Leu Cys<br>80                       85                     90                     95 | 290 |
| ttg gcg gcg tgc gag ctc gtc ggc ggc gac cga agc caa gcc atg gca<br>Leu Ala Ala Cys Glu Leu Val Gly Gly Asp Arg Ser Gln Ala Met Ala<br>                  100                    105                    110 | 338 |
| gcc gcg gcg gcg atc cat ctc gtg cac gcg gca gcc tac gtc cac gag<br>Ala Ala Ala Ala Ile His Leu Val His Ala Ala Ala Tyr Val His Glu<br>          115                      120                    125 | 386 |
| cac ctc cct cta acc gac ggg tcg agg ccc gta tcc aag ccc gca atc<br>His Leu Pro Leu Thr Asp Gly Ser Arg Pro Val Ser Lys Pro Ala Ile<br>        130                      135                    140 | 434 |
| cag cac aag tac ggc ccg aac gtc gag ctc ctc acc gga gac ggg att<br>Gln His Lys Tyr Gly Pro Asn Val Glu Leu Leu Thr Gly Asp Gly Ile<br>145                     150                    155 | 482 |
| gtc ccg ttc ggg ttt gag ttg ctg gcc ggg tca gtg gac ccg gcc cga<br>Val Pro Phe Gly Phe Glu Leu Leu Ala Gly Ser Val Asp Pro Ala Arg<br>160                     165                    170                    175 | 530 |
| aca gac gac ccg gat agg att ctg aga gtt ata ata gag atc agt cgg<br>Thr Asp Asp Pro Asp Arg Ile Leu Arg Val Ile Ile Glu Ile Ser Arg<br>        180                      185                    190 | 578 |
| gcc ggc ggg ccg gag gga atg ata agc ggg ctg cat agg gaa gaa gaa<br>Ala Gly Gly Pro Glu Gly Met Ile Ser Gly Leu His Arg Glu Glu Glu<br>          195                      200                    205 | 626 |
| att gtt gat gga aat acg agt tta gac ttc att gaa tat gtg tgc aag<br>Ile Val Asp Gly Asn Thr Ser Leu Asp Phe Ile Glu Tyr Val Cys Lys<br>        210                      215                    220 | 674 |
| aaa aaa tac ggc gag atg cat gct tgc ggc gcg gct tgt gga gcc ata<br>Lys Lys Tyr Gly Glu Met His Ala Cys Gly Ala Ala Cys Gly Ala Ile<br>225                     230                    235 | 722 |
| ttg ggc ggc gca gcc gag gag gag att cag aag ctg agg aat ttc ggg<br>Leu Gly Gly Ala Ala Glu Glu Glu Ile Gln Lys Leu Arg Asn Phe Gly<br>240                     245                    250                    255 | 770 |
| ctt tat caa gga act ctc aga gga atg atg gaa atg aaa aat tct cat<br>Leu Tyr Gln Gly Thr Leu Arg Gly Met Met Glu Met Lys Asn Ser His<br>                  260                    265                    270 | 818 |
| caa tta att gat gag aat ata att gga aaa ttg aaa gaa ttg gct ctc<br>Gln Leu Ile Asp Glu Asn Ile Ile Gly Lys Leu Lys Glu Leu Ala Leu<br>        275                      280                    285 | 866 |
| gag gag ttg gga ggc ttc cac ggg aag aac gct gag ctg atg tcg agc<br>Glu Glu Leu Gly Gly Phe His Gly Lys Asn Ala Glu Leu Met Ser Ser<br>          290                      295                    300 | 914 |
| ctt gta gcc gag ccg agc ctt tac gcg gct tagagctatt cggatccttc<br>Leu Val Ala Glu Pro Ser Leu Tyr Ala Ala<br>305                     310 | 964 |
| attgcatttt catgcgacat cttcatattc atattgcata atattttta agccagttat | 1024 |
| ttttttatta tgaattttt taactgttat tgatttcgaa aatactgaca atcatctaaa | 1084 |
| ataaagtaaa tatagtaagg atgaaaaaaa aaaaaaaaa aaaaaa | 1131 |

<210> SEQ ID NO 11
<211> LENGTH: 313
<212> TYPE: PRT
<213> ORGANISM: Mentha piperita

```
<400> SEQUENCE: 11

Met Ala Ile Asn Leu Ser His Ile Asn Ser Lys Thr Cys Phe Pro Leu
  1               5                  10                  15

Lys Thr Arg Ser Asp Leu Ser Arg Ser Ser Ala Arg Cys Met Pro
             20                  25                  30

Thr Ala Ala Ala Ala Phe Pro Thr Ile Ala Thr Ala Ala Gln Ser
             35                  40                  45

Gln Pro Tyr Trp Ala Ala Ile Glu Ala Asp Ile Glu Arg Tyr Leu Lys
             50                  55                  60

Lys Ser Ile Thr Ile Arg Pro Pro Glu Thr Val Phe Gly Pro Met His
 65                  70                  75                  80

His Leu Thr Phe Ala Ala Pro Ala Thr Ala Ala Ser Thr Leu Cys Leu
                 85                  90                  95

Ala Ala Cys Glu Leu Val Gly Gly Asp Arg Ser Gln Ala Met Ala Ala
                100                 105                 110

Ala Ala Ala Ile His Leu Val His Ala Ala Tyr Val His Glu His
             115                 120                 125

Leu Pro Leu Thr Asp Gly Ser Arg Pro Val Ser Lys Pro Ala Ile Gln
            130                 135                 140

His Lys Tyr Gly Pro Asn Val Glu Leu Leu Thr Gly Asp Gly Ile Val
145                 150                 155                 160

Pro Phe Gly Phe Glu Leu Leu Ala Gly Ser Val Asp Pro Ala Arg Thr
                165                 170                 175

Asp Asp Pro Asp Arg Ile Leu Arg Val Ile Glu Ile Ser Arg Ala
            180                 185                 190

Gly Gly Pro Glu Gly Met Ile Ser Gly Leu His Arg Glu Glu Ile
            195                 200                 205

Val Asp Gly Asn Thr Ser Leu Asp Phe Ile Glu Tyr Val Cys Lys Lys
210                 215                 220

Lys Tyr Gly Glu Met His Ala Cys Gly Ala Ala Cys Gly Ala Ile Leu
225                 230                 235                 240

Gly Gly Ala Ala Glu Glu Glu Ile Gln Lys Leu Arg Asn Phe Gly Leu
                245                 250                 255

Tyr Gln Gly Thr Leu Arg Gly Met Met Glu Met Lys Asn Ser His Gln
            260                 265                 270

Leu Ile Asp Glu Asn Ile Ile Gly Lys Leu Lys Glu Leu Ala Leu Glu
            275                 280                 285

Glu Leu Gly Gly Phe His Gly Lys Asn Ala Glu Leu Met Ser Ser Leu
    290                 295                 300

Val Ala Glu Pro Ser Leu Tyr Ala Ala
305                 310

<210> SEQ ID NO 12
<211> LENGTH: 8
<212> TYPE: PRT
<213> ORGANISM: Mentha piperita

<400> SEQUENCE: 12

Phe Gly Leu Tyr Gln Gly Thr Leu
  1               5

<210> SEQ ID NO 13
<211> LENGTH: 6
<212> TYPE: PRT
<213> ORGANISM: Mentha piperita
```

```
<400> SEQUENCE: 13

Val Ile Ile Glu Ile Ser
 1               5

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(18)
<223> OTHER INFORMATION: Forward PCR primer for cloning geranyl
      diphosphate synthase large subunit wherein n at position 9
      represents any nucleic acid base

<400> SEQUENCE: 14
aarccmacna aycayatg                                                    18

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(17)
<223> OTHER INFORMATION: Reverse PCR primer for cloning geranyl
      diphosphate synthase large subunit wherein n at position 6
      represents any nucleic acid base

<400> SEQUENCE: 15
ycrtgnggrt graartg                                                     17
```

GERANYL DIPHOSPHATE SYNTHASE LARGE SUBUNIT, AND METHODS OF USE

RELATED APPLICATIONS

The present application is a continuation-in-part of co-pending International patent application No. PCT/US98/21772, filed on Oct. 15, 1998, which is a continuation-in-part of U.S. patent application Ser. No. 08/951,924, filed on Oct. 16, 1997 (which issued as U.S. Pat. No. 5,876,964). The benefit of priority of each of the foregoing applications is claimed under 35 U.S.C. § 120, and each of the foregoing applications are incorporated herein by reference.

GOVERNMENT RIGHTS

This invention was funded by the United States Department of Energy grant number DE-FG03-96ER20212. The government has certain rights in the invention.

FIELD OF THE INVENTION

The present invention relates to nucleic acid sequences which code for geranyl diphosphate synthase large subunit, such as geranyl diphosphate synthase large subunit from *Mentha piperita*, and to vectors containing the sequences, host cells containing the sequences and methods of producing recombinant geranyl diphosphate synthase large subunit and its mutants.

BACKGROUND OF THE INVENTION

Geranyl diphosphate synthase (GPP synthase) is one of a family of enzymes called prenyltransferases that catalyze $C_5$ elongation reactions to form the linear (acyclic) precursors of the various terpenoid families. GPP synthase catalyzes the condensation of dimethylallyl diphosphate (DMAPP) and isopentenyl diphosphate (IPP) to form geranyl diphosphate (GPP) which is the immediate, $C_{10}$ acyclic precursor of the monoterpenes (Wise, M. L. and Croteau, R., in Cane, D. E., ed., "Comprehensive Natural Products Chemistry: Isoprenoids, Vol. 2", Elsevier Science, Oxford, 1999. ps. 97–154) (FIG. 1). Farnesyl diphosphate synthase (FPP synthase), a related prenyltransferase, utilizes GPP and IPP as substrates to form farnesyl diphosphate (FPP), which is the immediate, $C_{15}$ precursor of the sesquiterpenes (FIG. 1). Another prenyltransferase, geranylgeranyl diphosphate synthase (GGPP synthase), catalyzes the condensation of farnesyl diphosphate (or DMAPP) and IPP to form geranylgeranyl diphosphate (GGPP) which is the immediate $C_{20}$ precursor of the diterpene family (FIG. 1). Other types of prenyltransferases can utilize FPP, GGPP and IPP as substrates to form very long chain molecules, such as natural rubber. Poulter C. D. and Rilling, H. C., *Accts. Chem. Res.* 11: 307–313 (1978); Scolnik, P. A. and Bartley, G., *Plant Mol Biol. Rep.* 14: 305, 307 (1996); Ogura, K. and Koyama, T., *Chem. Rev.* 98: 1263–1276 (1998).

The basic reaction mechanism for all of these prenyltransferases is the same, and consists of three steps (see FIG. 2 in which the reaction catalyzed by geranyl diphosphate synthase is presented as illustrative of the general reaction mechanism). With reference to FIG. 2, in the first step an allylic diphosphate ester (2a) is ionized to the stable carbonium ion (2b). The carbonium ion then attacks the double bond of isopentenyl diphosphate (2c) to yield another carbonium ion (2d). In the final step of the cycle, a proton is eliminated from the newly formed carbonium ion (2d) to form a terpenoid containing a new allylic double bond (2e). In the reaction catalyzed by GPP synthase, the allylic diphosphate ester is dimethyl allyl diphosphate (FIG. 1 and FIG. 2). In the reactions catalyzed by FPP synthase and GGPP synthase the allylic diphosphate ester is geranyl diphosphate and farnesyl diphosphate, respectively (FIG. 1).

Unlike FPP synthase and GGPP synthase, which produce GPP as an intermediate and which are nearly ubiquitous (Ogura, K. and Koyama, T., in Ogura, K. and Sankawa, U., eds., "Dynamic Aspects of Natural Products Chemistry" Kodansha/Harwood Academic Publishers, Tokyo, pp. 1–23, 1997), geranyl diphosphate synthase is largely restricted to plant species that produce abundant quantities of monoterpenes. Because both FPP synthase and GGPP synthase produce only negligible levels of GPP as a free intermediate on route to FPP and GGPP ((Ogura, K. and Koyama, T., in Ogura, K. and Sankawa, U., eds., "Dynamic Aspects of Natural Products Chemistry" Kodansha/Harwood Academic Publishers, Tokyo, pp. 1–23, 1997)), it is geranyl diphosphate synthase that provides the crucial link between primary metabolism and monoterpene biosynthesis and that serves as the essential driver of monoterpene biosynthesis (Wise, M. L. and Croteau, R., supra).

Any attempt, therefore, to exploit recombinant methods to increase the yield of monoterpene-producing (essential oil) species, or to genetically engineer the monoterpene biosynthetic pathway into any non-producing species (e.g., field crops, fruit-bearing plant species and animals) requires access to a geranyl diphosphate synthase gene or cDNA clone. Co-expression of geranyl diphosphate synthase along with a selected monoterpene synthase, such as (−)-limonene synthase (Colby et al., *J Biol. Chem.* 268:23016–23024, 1993), and any subsequent pathway enzymes, should allow production of the corresponding monoterpene product(s) from simple carbon substrates, such as glucose, in any living organism.

Monoterpenes are utilized as flavoring agents in food products, and as scents in perfumes (Arctander, S., in *Perfume and Flavor Materials of Natural Origin*, Arctander Publications, Elizabeth, N.J.; Bedoukian, P. Z. in *Perfumery and Flavoring* Materials, 4th edition, Allured Publications, Wheaton, Ill., 1995; Allured, S., in *Flavor and Fragrance Materials*, Allured Publications, Wheaton, Ill., 1997. Monoterpenes are also used as intermediates in various industrial processes. Dawson, F. A., in *The Amazing Terpenes*, Naval Stores Rev., Mar./Apr., 6–12, 1994. Monoterpenes are also implicated in the natural defense systems of plants against pests and pathogens. Francke, W. in Muller, P. M. and Lamparsky, D., eds., *Perfumes: Art, Science and Technology*, Elsevier Applied Science, NY, N.Y., 61–99, 1991; Harborne, J. B., in Harborne, J. B. and Tomas-Barberan, F. A., eds., Ecological Chemistry and Biochemistry of Plant Terpenoids, Clarendon Press, Oxford, 399–426, 1991; Gershenzon, J and Croteau, R in Rosenthal, G. A. and Berenbaum, M. R., eds., Herbivores: Their Interactions with Secondary Plant Metabolites, Academic Press, San Diego, 168–220, 1991.

There is also substantial evidence that monoterpenes are effective in the prevention and treatment of cancer (Elson, C. E. and Yu, S. G., *J Nutr.* 124: 607–614, 1994.). Thus, for example, limonene, perrilyl alcohol and geraniol have each been shown to have chemotherapeutic activity against a very broad range of mammalian cancers (see, for example, (1) limonene, Elegbede et al., *Carcinogenesis* 5:661–665, 1984; Elson et al., *Carcinogenesis* 9:331–332, 1988; Maltzman et al., *Carcinogenesis* 10:781–785, 1989; Wattenberg, L. W. and Coccia, J. B., *Carcinogenesis* 12:115–117, 1991; Wattenberg, L. W. and Coccia, J. B., *Carcinogenesis* 12:115–117, 1991; Haag et al., *Cancer Res.* 52:4021–4026, 1992; Crowell, P. L. and Gould, M. N., *CRC Crit. Rev. Oncogenesis* 5:1–22, 1994; (2) perillyl alcohol, Mills et al., *Cancer Res.* 55:979–983, 1995; Haag, J. D. and Gould, M. N., *Cancer Chemother. Pharmacol.* 34:477–483, 1994; Stark et al., *Cancer Lett.* 96:15–21, 1995 and (3) geraniol, Shoff et al., *Cancer Res.* 51:37–42, 1991; Yu et al., *J. Nutr.* 125:2763–2767, 1995; Burke et al., *Lipids* 32:151–156, 1997.).

Cancer cells can be modified to produce therapeutic amounts of a monoterpene having anti-cancer properties by targeting the cognate monoterpene synthase protein to cancer cells, or by introducing a monoterpene synthase gene into cancer cells. This approach to cancer therapy is complicated, however, by the fact that the natural distribution of geranyl diphosphate synthase is largely restricted to plant species that produce abundant quantities of monoterpenes. Thus, animal cells do not naturally produce the monoterpene precursor geranyl diphosphate. Consequently, the genetic manipulation of cancer cells to produce endogenous monoterpenes having anti-cancer properties requires the introduction of a gene encoding geranyl diphosphate synthase, together with a gene encoding a monoterpene synthase that produces a monoterpene having anti-cancer properties. Similarly, if the protein targeting approach is utilized, both geranyl diphosphate synthase protein and monoterpene synthase protein must be targeted to cancer cells.

Standard protein targeting techniques can be used to introduce geranyl diphosphate synthase along with a monoterpene synthase, such as limonene synthase (Colby et al., *J. Biol. Chem.* 268:23016–23024, 1993), into animal cells with specific targeting to tumors. See, e.g., Wearley, L. L., *Critical Reviews in Therapeutic Drug Carrier Systems*, 8(4): 331–394, 1991; Sheldon, K et al., *Proc. Nat'l. Acad. Sci. USA.*, 92(6): 2056–2060, 1995. In addition, standard gene therapy techniques can be used to target a GPP synthase gene and a monoterpene synthase gene to cancerous cells for endogenous synthesis of monoterpenes having anti-cancer properties. For reviews of gene targeting technology see; Mahato R. I et al., *Pharmaceutical Research* 14(7): 853–859, 1997; Rosenthal, F. M. and Mertelsmann, R., *Onkologie* 20(1): 26–34, 1997; Buckel, P., *Trends in Pharmacological Sciences* 17(12): 450–456, 1996; Roth, J. A. and Cristiano, R. J., *J. Nat'l Cancer Inst.* 89(1): 21–39, 1997; Ledley, F. D, *Pharmaceutical Research* 13(11): 1595–1614, 1996.

To date, extracts containing geranyl diphosphate synthase activity have been isolated from several plant sources, including grape (Clastre et al., *Plant Physiol.* 102:205–211, 1993); geranium (Suga, T. and Endo, T., *Phytochemistry* 30:1757–1761, 1991); sage (Croteau, R. and Purkett, P. T., *Arch. Biochem. Biophys.* 271:524–535, 1989) and *Lithospermum* (Heide, L. and Berger, U., *Arch Biochem. Biophys.* 273:331–338, 1989). Only the enzyme from grape has been purified to homogeneity (Clastre et al., supra). The structures and properties of prenyltransferase enzymes and genes are reviewed in, K. Ogura and T. Koyama, *Chem. Rev.* 98:1263–1276 (1998), and in T. Koyama and K. Ogura, "Isopentenyl Diphosphate Isomerase and Prenyltransferases," in Cane, D.E., ed., *Comprehensive Natural Products Chemistry: Isoprenoids*, Vol. 2, Elsevier Science, Oxford, 1999, pp. 69–96.

U.S. patent Ser. No. 5,876,964 and copending, international patent application PCT/US98/21772, each disclose the isolation and sequence of cDNA molecules encoding what was initially characterized as a geranyl diphosphate synthase protein. The putative geranyl diphosphate synthase protein exhibited only a small fraction of the biological activity of native geranyl diphosphate synthase extracted from plant tissue. In view of the disclosure of the present patent application, the putative geranyl diphosphate synthase protein disclosed in U.S. patent Ser. No. 5,876,964, and in copending, international patent application PCT/US98/21772, is now known to be the small subunit of geranyl diphosphate synthase which exists, in its native, fully functional form, as a heterodimer including a small subunit and a large subunit. The present patent application discloses the isolation and sequence of a Mentha cDNA encoding geranyl diphosphate synthase large subunit, and enables the isolation of additional nucleic acid molecules encoding geranyl diphosphate synthase large subunit.

SUMMARY OF THE INVENTION

In accordance with the foregoing, a cDNA encoding geranyl diphosphate synthase large subunit from peppermint has been isolated and sequenced, and the corresponding amino acid sequence has been deduced. Accordingly, the present invention relates to isolated, recombinant geranyl diphosphate synthase large subunit proteins, to isolated DNA sequences which code for the expression of geranyl diphosphate synthase large subunit, such as the sequence designated SEQ ID NO:1 which encodes geranyl diphosphate synthase large subunit (SEQ ID NO:2) from peppermint (*Mentha piperita*). In other aspects, the present invention is directed to replicable recombinant cloning vehicles comprising a nucleic acid sequence, e.g., a DNA sequence which codes for a geranyl diphosphate synthase large subunit or for a base sequence sufficiently complementary to at least a portion of the geranyl diphosphate synthase large subunit DNA or RNA to enable hybridization therewith (e.g., antisense geranyl diphosphate synthase large subunit RNA or fragments of complementary geranyl diphosphate synthase large subunit DNA which are useful as polymerase chain reaction primers or as probes for geranyl diphosphate synthase large subunit genes, or related genes). In yet other aspects of the invention, modified host cells are provided that have been transformed, transfected, infected and/or injected with a recombinant cloning vehicle and/or DNA sequence of the invention. Thus, the present invention provides for the recombinant expression of geranyl diphosphate synthase large subunit. The inventive concepts described herein may be used to facilitate the production, isolation and purification of significant quantities of recombinant geranyl diphosphate synthase large subunit for subsequent use, to obtain expression or enhanced expression of geranyl diphosphate synthase large subunit in plants, microorganisms or animals, or may be otherwise employed in an environment where the regulation or expression of geranyl diphosphate synthase large subunit is desired, for example for the production of the enzyme product of geranyl diphosphate synthase heterodimer, geranyl diphosphate, or its derivatives.

In another aspect, the present invention provides isolated, recombinant geranyl diphosphate synthase heterodimer protein comprising an isolated, X recombinant geranyl diphosphate synthase large subunit protein and an isolated, recombinant geranyl diphosphate synthase small subunit protein.

In yet another aspect of the present invention, methods are provided for treating cancer. The cancer treatment methods include the step of introducing a geranyl diphosphate synthase small subunit protein into a cancer cell, together with a monoterpene synthase protein that is capable of converting geranyl diphosphate to a monoterpene having anticancer properties. More preferably, nucleic acid sequences encoding a geranyl diphosphate synthase small subunit protein and a monoterpene synthase protein (that is capable of converting geranyl diphosphate to a monoterpene having anticancer properties) are introduced into a cancer cell under conditions that enable expression of the geranyl diphosphate synthase small subunit and monoterpene synthase proteins. It is understood that a single nucleic acid molecule can encode both the geranyl diphosphate synthase small subunit and monoterpene synthase proteins.

In a presently preferred embodiment, the cancer treatment methods of the present invention include the step of introducing a geranyl diphosphate synthase large subunit protein and a geranyl diphosphate synthase small subunit protein into a cancer cell, together with a monoterpene synthase protein that is capable of converting geranyl diphosphate to a monoterpene having anticancer properties. More preferably, nucleic acid molecules encoding a geranyl diphosphate synthase small subunit protein, a geranyl diphosphate synthase large subunit protein and a monoterpene synthase protein (that is capable of converting geranyl diphosphate to a monoterpene having anticancer properties) are introduced into a cancer cell under conditions that enable expression of the geranyl diphosphate synthase small subunit, large subunit and monoterpene synthase proteins. It is understood that a single nucleic acid molecule can encode the geranyl diphosphate synthase small subunit, the geranyl diphosphate synthase large subunit and monoterpene synthase proteins.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
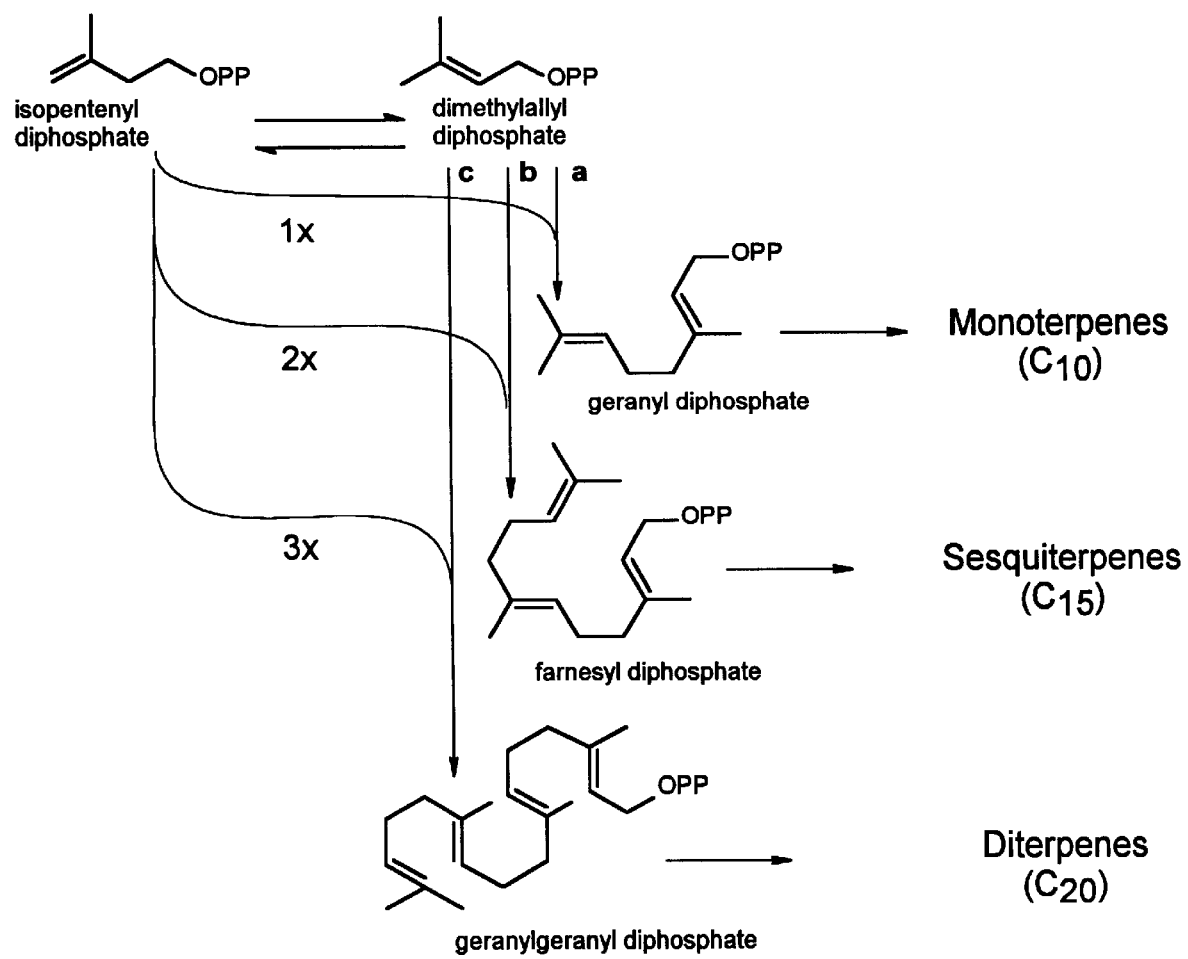
FIG. 1 shows the condensation reactions catalyzed by (a) geranyl diphosphate synthase, (b) farnesyl diphosphate synthase and (c) geranylgeranyl diphosphate synthase.
Figure 2:
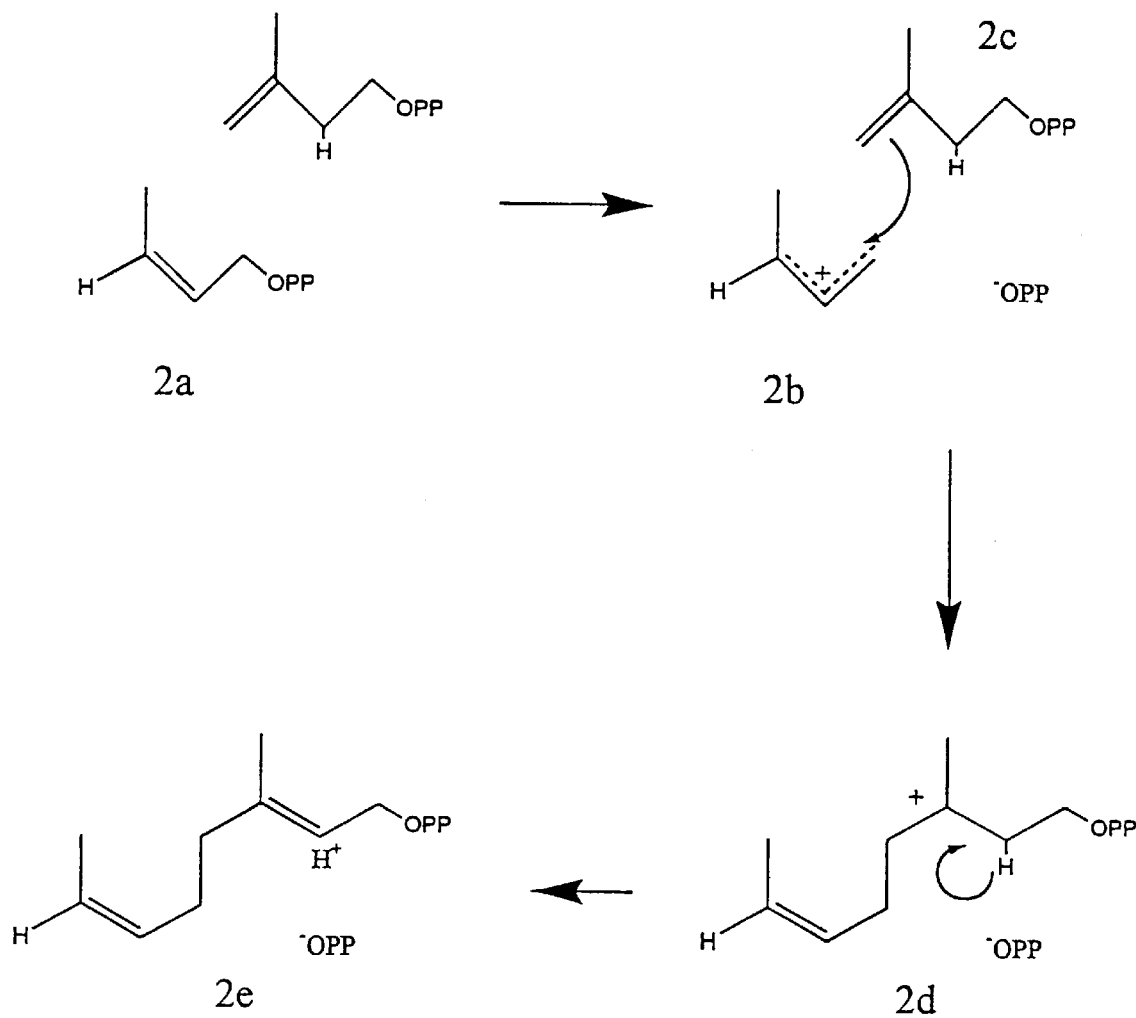
FIG. 2 shows the reaction mechanism common to all prenyltransferases. The reaction catalyzed by geranyl diphosphate synthase is presented as illustrative of the general mechanism.

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
|---|---|---|---|---|---|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

The term "percent identity" (%I) means the percentage of amino acids or nucleotides that occupy the same relative position when two amino acid sequences, or two nucleic acid sequences, are aligned side by side.

The term "percent similarity" (%S) is a statistical measure of the degree of relatedness of two compared protein sequences. The percent similarity is calculated by a computer program that assigns a numerical value to each compared pair of amino acids based on observed amino acid replacements in closely related sequences. Calculations are made after a best fit alignment of the two sequences has been made empirically by iterative comparison of all possible alignments. (Henikoff, S. and Henikoff, J. G., *Proc. Nat'l Acad Sci USA* 89: 10915–10919, 1992).

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "geranyl diphosphate synthase" is used herein to mean an enzyme capable of catalyzing the condensation of dimethylallyl diphosphate (DMAPP) and isopentenyl diphosphate (IPP) to form geranyl diphosphate, the immediate acyclic precursor of the monoterpenes, as described herein. In its fully-functional, naturally-occurring form, geranyl diphosphate synthase exists as heterodimer composed of a geranyl diphosphate synthase large subunit and a geranyl diphosphate synthase small subunit.

The term "essential oil plant," or "essential oil plants," refers to a group of plant species that produce high levels of monoterpenoid and/or sesquiterpenoid and/or diterpenoid oils, and/or high levels of monoterpenoid and/or sesquiterpenoid and/or diterpenoid resins. The foregoing oils and/or resins account for greater than about 0.005% of the fresh weight of an essential oil plant that produces them. The essential oils and/or resins are more fully described, for example, in E. Guenther, The Essential Oils, Vols. I–VI, R. E. Krieger Publishing Co., Huntington N.Y., 1975, incorporated herein by reference. The essential oil plants include, but are not limited to:

Lamiaceae, including, but not limited to, the following species: Ocimum (basil), Lavandula (Lavender), Origanum (oregano), Mentha (mint), Salvia (sage), Rosmarinus (rosemary), Thymus (thyme), Satureja and Monarda.

Umbelliferae, including, but not limited to, the following species: Carum (caraway), Anethum (dill), feniculum (fennel) and Daucus (carrot).

Asteraceae (Compositae), including, but not limited to, the following species: Artemisia (tarragon, sage brush), Tanacetum (tansy).

Rutaceae (e.g., citrus plants); Rosaceae (e.g., roses); Myrtaceae (e.g., eucalyptus, Melaleuca); the Gramineae (e.g., Cymbopogon (citronella)); Geranaceae (Geranium) and certain conifers including Abies (e.g., Canadian balsam), Cedrus (cedar), Thuja, Pinus (pines) and Juniperus.

The range of essential oil plants is more fully set forth in *E. Guenther, The Essential Oils, Vols.* I–VI, R. E. Krieger Publishing Co., Huntington N.Y, 1975, which is incorporated herein by reference.

The term "angiosperm" refers to a class of plants that produce seeds that are enclosed in an ovary.

The term "gymnosperm" refers to a class of plants that produce seeds that are not enclosed in an ovary.

The terms "alteration", "amino acid sequence alteration", "variant" and "amino acid sequence variant" refer to geranyl diphosphate synthase large subunit molecules with some differences in their amino acid sequences as compared to native geranyl diphosphate synthase large subunit. Ordinarily, the variants will possess at least about 70% homology with native geranyl diphosphate synthase large subunit, and preferably they will be at least about 80% homologous with native geranyl diphosphate synthase large subunit. The amino acid sequence variants of geranyl diphosphate synthase large subunit falling within this invention possess substitutions, deletions, and/or insertions at certain positions. Sequence variants of geranyl diphosphate synthase large subunit may be used to attain desired enhanced or reduced enzymatic activity, or altered substrate utilization or product distribution of the geranyl diphosphate synthase heterodimer.

Substitutional geranyl diphosphate synthase large subunit variants are those that have at least one amino acid residue in the native geranyl diphosphate synthase large subunit sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the geranyl diphosphate synthase large subunit molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the geranyl diphosphate synthase large subunit molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional geranyl diphosphate synthase large subunit variants are those with one or more amino acids inserted immediately adjacent to an amino acid at a particular position in the native geranyl diphosphate synthase large subunit molecule. Immediately adjacent to an amino acid means connected to either the a-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native geranyl diphosphate synthase large subunit molecule have been removed. Ordinarily, deletional variants will have one or two amino acids deleted in a particular region of the geranyl diphosphate synthase large subunit molecule.

The terms "biological activity", "biologically active", "activity" and "active," when used with reference to geranyl diphosphate synthase, refer to the ability of the geranyl diphosphate synthase heterodimer to condense dimethylallyl diphosphate (DMAPP) and isopentenyl diphosphate (IPP) to form geranyl diphosphate, as measured in an enzyme activity assay, such as the assay described in Example 1 below. Amino acid sequence variants of geranyl diphosphate synthase (i.e., amino acid sequence variants of either or both of the large subunit or the small subunit) may have desirable, altered biological activity including, for example, altered reaction kinetics, substrate utilization product distribution or other characteristics.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, a cDNA encoding geranyl diphosphate synthase large subunit was isolated and sequenced in the following manner. Geranyl diphosphate synthase large subunit is located exclusively in the glandular trichome secretory cells and interacts with geranyl diphosphate synthase small subunit to form geranyl diphosphate synthase which catalyzes the formation of geranyl diphosphate in these essential oil species. These secretory cell clusters were isolated from *Mentha spicata* and geranyl diphosphate synthase large subunit was purified therefrom utilizing a purification protocol consisting of a dye-ligand chromatography step, and an anion exchange chromatography step followed by preparative SDS-PAGE. The limited amount of purified geranyl diphosphate synthase large subunit yielded six peptide fragments when digested with trypsin, and the sequence of four of these peptide fragments was determined, peptide 1 (SEQ ID NO:3), peptide 2 (SEQ ID NO:4), peptide 3 (SEQ ID NO:5) and peptide 4 (SEQ ID NO:6). This sequence information was insufficient to permit a reverse genetic approach to cloning the geranyl diphosphate synthase large subunit cDNA, i.e., there was insufficient amino acid sequence to permit the construction of degenerate oligonucleotide probes that were sufficiently specific to be effective as probes (these sequences were too degenerate to permit the design of specific PCR primers).

Consequently, total RNA was extracted from isolated trichome secretory cells derived from Mentha piperita and mRNA was purified therefrom. The secretory cell MRNA served as the substrate for the synthesis of a cDNA library by standard means. One hundred and thirty, randomly selected cDNA clones were sequenced and one clone showed homology to plant-derived geranylgeranyl diphosphate synthases (~67–83% identity; ~74–93% similarity). Sequence information derived from this "prenyltransferase-like" cDNA was used to construct PCR primers GG23F (SEQ ID NO:7) and GG23R (SEQ ID NO:8) which were, in turn, used to amplify a 101 bp fragment (SEQ ID NO:9) of the 5'-end of the geranylgeranyl diphosphate synthase-like cDNA. The 101 bp fragment (SEQ ID NO:9) was radiolabelled and used as a probe to screen a mint oil gland cDNA library. Ten positive clones were purified through a second round of screening and were sequenced to yield the full-length cDNA insert of pMp23.10 (SEQ ID NO:1). This clone was initially considered to encode geranylgeranyl diphosphate synthase, but the expressed protein (SEQ ID NO:2) did not yield a functional GGPP synthase; however, alignment of the four peptide sequences, derived from the purified 37 kDa protein, obtained by purification of mint geranyl diphosphate synthase, with the deduced amino acid sequence of pMp23.10 (SEQ ID NO:2), revealed that peptide 1 (LIGVE) (SEQ ID NO:3) corresponded exactly to deduced amino acid residues 333 to 337 of SEQ ID NO:2, that peptide 2 (YIAYR) (SEQ ID NO:4) corresponded exactly to deduced amino acid residues 371 to 375 of SEQ ID NO:2, that peptide 3 (TAALLTGSVVLGAIL) (SEQ ID NO:5) corresponded to residues 263 to 277 of SEQ ID NO:2 and peptide 4 (EAVETLLHF) (SEQ ID NO:6) to residues 349–357 of SEQ ID NO:2. These results suggested that the nucleic acid molecule of SEQ ID NO: 1 encoded a GPP synthase.

Cell-free extracts of bacteria harboring both a geranyl diphosphate synthase large subunit clone (SEQ ID NO:1) and a geranyl diphosphate synthase small subunit clone (SEQ ID NO:10), encoding the protein of SEQ ID NO:11 (the geranyl diphosphate synthase small subunit clone is designated Mp13.18, and is fully disclosed and described in U.S. patent Ser. No. 5,876,964 and in copending, international patent application PCT/US98/21772, both of which are incorporated herein by reference) yielded levels of prenyltransferase activity significantly higher than the corresponding empty vector controls, and separation of activities by ion-exchange chromatography revealed the presence of a prenyltransferase that eluted at >90 mM KCl and that was absent in preparations from the controls. This new, recombinant prenyltransferase was confirmed to be geranyl diphosphate synthase by radio-gas chromatographic analysis demonstrating the exclusive production of the $C_{10}$ product.

The isolation of a cDNA encoding geranyl diphosphate synthase large subunit permits the development of an efficient expression system for this protein, provides a useful tool for examining the developmental regulation of monoterpene biosynthesis and permits the isolation of other geranyl diphosphate synthase large subunits. The isolation of a geranyl diphosphate synthase large subunit cDNA also permits the transformation of a wide range of organisms in order to introduce monoterpene biosynthesis de novo, or to modify endogenous monoterpene biosynthesis. Further, the isolation of a geranyl diphosphate synthase large subunit cDNA also permits coexpression of the large and small subunits of geranyl diphosphate synthase in a host cell to form fully functional, recombinant geranyl diphosphate synthase heterodimer.

Although the geranyl diphosphate synthase large subunit protein set forth in SEQ ID NO:2 directs the enzyme to plastids, substitution of the putative targeting sequence (SEQ ID NO:2, amino acids 1 to 48) with other transport sequences well known in the art (see, e.g., von Heijne G et al., Eur. J. Biochem 180: 535–545, 1989; Stryer, Biochemistry W. H. Freeman and Company, New York, N.Y., p. 769 [1988]) may be employed to direct the geranyl diphosphate synthase large subunit to other cellular or extracellular locations.

In addition to the native geranyl diphosphate synthase large subunit amino acid sequence of SEQ ID NO:2 encoded by the cDNA insert of plasmid Mp 23.10 (SEQ ID NO:1), sequence variants produced by deletions, substitutions, mutations and/or insertions are intended to be within the scope of the invention except insofar as limited by the prior art. Geranyl diphosphate synthase large subunit amino acid sequence variants may be constructed by mutating the DNA sequence that encodes wild-type geranyl diphosphate synthase large subunit, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of E. coli. Plasmid DNA is isolated from the transformed bacteria, restricted with the relevant restriction enzyme (thereby linearizing the unmutated plasmids), and then retransformed into E. coli. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes can be cloned into a replicable expression vector, if not already cloned into a vector of this type, and the resulting expression construct used to transform E. coli, such as strain E. coli BL21(DE3)pLysS, for high level production of the mutant protein, and subsequent purification thereof. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutant, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that will be altered, although aromatics can also be substituted for alkyl side chains. Changes in the normal product distribution can indicate which step(s) of the reaction sequence have been altered by the mutation.

Other site directed mutagenesis techniques may also be employed with the nucleotide sequences of the invention. For example, restriction endonuclease digestion of DNA followed by ligation may be used to generate geranyl diphosphate synthase large subunit deletion variants, as described in section 15.3 of Sambrook et al. (*Molecular Cloning: A Laboratory Manual*, 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (DNA 2:183 [1983]). Generally, oligonucleotides of at least 25 nucleotides in length are used to insert, delete or substitute two or more nucleotides in the geranyl diphosphate synthase large subunit molecule. An optimal oligonucleotide will have 12 to 15 perfectly matched nucleotides on either side of the nucleotides coding for the mutation. To mutagenize the wild-type geranyl diphosphate synthase large subunit, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type geranyl diphosphate synthase large subunit inserted in the vector, and the second strand of DNA encodes the mutated form of geranyl diphosphate synthase large subunit inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type geranyl diphosphate synthase large subunit DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

The gene, or other nucleic acid molecule, encoding geranyl diphosphate synthase large subunit may be incorporated, together with a nucleic acid molecule encoding geranyl diphosphate synthase small subunit (separately or operationally linked), into any organism (intact plant, animal, microbe), or cell culture derived therefrom, that produces dimethylallyl diphosphate and isopentenyl diphosphate to effect the conversion of these primary substrates to geranyl diphosphate and its subsequent metabolic products, depending on the organism. The geranyl diphosphate synthase large subunit gene, together with a nucleic acid molecule encoding geranyl diphosphate synthase small subunit, may be introduced into any organism for a variety of purposes including, but not limited to: production or modification of flavor and aroma properties; improvement of defense capability; the alteration of other ecological interactions mediated by geranyl diphosphate and its derivatives; selective destruction or inhibition of the growth, development or division of cancerous cells; or the production of geranyl diphosphate and its derivatives.

Eukaryotic expression systems may be utilized for geranyl diphosphate synthase large subunit production since they are capable of carrying out any required posttranslational modifications and of directing the enzyme to the proper membrane location. A representative eukaryotic expression system for this purpose uses the recombinant baculovirus, Autographa californica nuclear polyhedrosis virus (AcNPV;

M. D. Summers and G. E. Smith, *A Manual of Methods for Baculovirus Vectors and Insect Cell Culture Procedures* [1986]; Luckow et al., *Bio-technology* 6:47–55 [1987]) for expression of the geranyl diphosphate synthase large subunit of the invention. Infection of insect cells (such as cells of the species *Spodoptera frugiperda*) with the recombinant baculoviruses allows for the production of large amounts of the geranyl diphosphate synthase large subunit protein. In addition, the baculovirus system has other important advantages for the production of recombinant geranyl diphosphate synthase large subunit. For example, baculoviruses do not infect humans and can therefore be safely handled in large quantities. In the baculovirus system, a DNA construct is prepared including a DNA segment encoding geranyl diphosphate synthase large subunit and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/geranyl diphosphate synthase large subunit (and/or small subunit) combination is flanked on both sides by 200–300 base pairs of baculovirus DNA (the flanking sequences).

To produce the geranyl diphosphate synthase large subunit DNA construct, a cDNA clone encoding the full length geranyl diphosphate synthase large subunit is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full geranyl diphosphate synthase large subunit. For example, an insect host cell can be cotransfected or transfected separately with the DNA construct and a functional baculovirus. Resulting recombinant baculoviruses can then be isolated and used to infect cells to effect production of the geranyl diphosphate synthase large subunit. Host insect cells include, for example, *Spodoptera frugiperda* cells, that are capable of producing a baculovirus-expressed geranyl diphosphate synthase large subunit. Insect host cells infected with a recombinant baculovirus of the present invention are then cultured under conditions allowing expression of the baculovirus-encoded geranyl diphosphate synthase large subunit. Geranyl diphosphate synthase large subunit thus produced is then extracted from the cells using methods known in the art.

Other eukaryotic microbes such as yeasts may also be used to practice this invention. The baker's yeast *Saccharomyces cerevisiae*, is a commonly used yeast, although several other types are available. The plasmid YRp7 (Stinchcomb et al., *Nature* 282:39 [1979]; Kingsman et al., *Gene* 7:141 [1979]; Tschemper et al., *Gene* 10:157 [1980]) is commonly used as an expression vector in Saccharomyces. This plasmid contains the trp1 gene that provides a selection marker for a mutant strain of yeast lacking the ability to grow in the absence of tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad Sci. USA* 75:1929 [1978]. Additional yeast transformation protocols are set forth in Gietz et al., *N.A.R.* 20(17):1425, 1992; Reeves et al., *FEMS* 99:193–197, 1992.

Suitable promoting sequences in yeast vectors include the promoters for 3-phosphoglycerate kinase (Hitzeman et al., *J Biol. Chem.* 255:2073 [1980]) or other glycolytic enzymes (Hess et al., *J Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode geranyl diphosphate synthase large subunit and a selectable marker gene, e.g., the kan gene encoding resistance to kanamycin, into *Agrobacterium tumifaciens* containing a helper Ti plasmid as described in Hoeckema et al., *Nature* 303:179–181 [1983] and culturing the Agrobacterium cells with leaf slices of the plant to be transformed as described by An et al., *Plant Physiology* 81:301–305 [1986]. Transformation of cultured plant host cells is normally accomplished through *Agrobacterium tumifaciens*, as described above. Cultures of mammalian host cells and other host cells that do not have rigid cell membrane barriers are usually transformed using the calcium phosphate method as originally described by Graham and Van der Eb (Virology 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffler, *Proc. Natl. Acad. Sci. USA* 77:2163 [1980]), electroporation (Neumann et al., *EMBO J.* 1:841 [1982]), and direct microinjection into nuclei (Capecchi, Cell 22:479 [1980]) may also be used. Additionally, animal transformation strategies are reviewed in Monastersky G. M. and Robl, J. M., *Strategies in Transgenic Animal Science*, ASM Press, Washington, D.C., 1995. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating geranyl diphosphate synthase large subunit production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a geranyl diphosphate synthase large subunit gene that previously has had its native promoter removed. This engineered gene is the combination of a promoter that responds to an external chemical stimulus and a gene responsible for successful production of geranyl diphosphate synthase large subunit.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993], incorporated by reference herein). Representative examples include electroporation-facilitated DNA uptake by protoplasts in which an electrical pulse transiently permeabilizes cell membranes, permitting the uptake of a variety of biological molecules, including recombinant DNA (Rhodes et al., *Science*, 240:204–207 [1988]); treatment of protoplasts with polyethylene glycol (Lyznik et al., *Plant Molecular Biology*, 13:151–161 [1989]); and bombardment of cells with DNA-laden microprojectiles which are propelled by explosive force or compressed gas to penetrate the cell wall (Klein et al., *Plant Physiol.* 91:440–444 [1989] and Boynton et al., *Science*, 240:1534–1538 [1988]). Transformation of Taxus species can be achieved, for example, by employing the methods set forth in Han et al, *Plant Science*, 95:187–196 (1994), incorporated by reference herein. A method that has been applied to Rye plants (*Secale cereale*) is to directly inject plasmid DNA, including a selectable marker gene, into developing floral tillers (de la Pena et al., *Nature* 325:274–276 (1987)). Further, plant viruses can be used as vectors to transfer genes to plant cells. Examples of plant viruses that can be used as vectors to transform plants include the Cauliflower Mosaic Virus (Brisson et al., *Nature* 310: 511–514 (1984); Additionally, plant transformation strategies and techniques are reviewed in Birch, R. G., *Ann Rev Plant Phys Plant Mol Biol*, 48:297 (1997); Forester et al., *Exp. Agric.*, 33:15–33 (1997). The aforementioned publications disclosing plant transformation techniques are incorporated herein by reference, and minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J Gen. Virol.* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, Biol. Reprod. 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J Cell Biol.* 85:1 [1980]); and TRI cells (Matheretal., *Annals N.Y Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of geranyl diphosphate synthase large subunit in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wildtype DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC No. 31,446), *E. coli* strain W3110 (ATCC No. 27,325) *E. coli* XI 1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275–296, Plenum Publishing Corp., 1990; Hanahan et al., *Meth. Enxymol*, 204:63, 1991.

As a representative example, cDNA sequences encoding geranyl diphosphate synthase large subunit may be transferred to the $(His)_6$•Tag pET vector commercially available (from Novagen) for overexpression in *E. coil* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the geranyl diphosphate synthase large subunit again purified by immobilized metal ion affinity chromatography, this time using a shallower imidazole gradient to elute the recombinant synthase while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and BluescriptM13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl Acids Res*. 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W.H. Freeman and Company, New York, N.Y., p. 769 [1988]), and can be used as signal sequences in appropriate eukaryotic host cells. Yeast signal sequences, as for example acid phosphatase (Arima et al., Nuc. Acids Res. 11:1657 [1983]), alpha-factor, alkaline phosphatase and invertase may be used to direct secretion from yeast host cells. Prokaryotic signal sequences from genes encoding, for example, LamB or OmpF (Wong et al., Gene 68:193 [1988]), MalE, PhoA, or beta-lactamase, as well as other genes, may be used to target proteins from prokaryotic cells into the culture medium.

The geranyl diphosphate synthase large subunit protein having the sequence set forth in SEQ ID NO:2 includes a putative amino terminal membrane insertion sequence at residues 1 through 48, and in the embodiment shown in SEQ ID NO:2 directs the enzyme to plastids. Alternative trafficking sequences from plants, animals and microbes can be employed in the practice of the invention to direct the gene product to the cytoplasm, endoplasmic reticulum, mitochondria or other cellular components, or to target the protein for export to the medium. These considerations apply to the overexpression of geranyl diphosphate synthase large subunit, and to direction of expression within cells or intact organisms to permit gene product function in any desired location.

The construction of suitable vectors containing DNA encoding replication sequences, regulatory sequences, phenotypic selection genes and the geranyl diphosphate synthase large subunit DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, geranyl diphosphate synthase large subunit variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

In another aspect of the invention, a nucleic acid molecule encoding geranyl diphosphate synthase large subunit may be introduced into cancerous cells, together with a nucleic acid molecule encoding geranyl diphosphate synthase small subunit and a nucleic acid molecule encoding a monoterpene synthase that produces a monoterpene having anti-cancer properties. Nucleic acid molecules encoding geranyl diphosphate synthase large subunit and small subunit (or a single nucleic acid molecule encoding both large and small subunits) must be introduced into cancerous cells, in addition to a gene encoding a monoterpene synthase producing a monoterpene having anti-cancer properties, because animal cells do not naturally produce geranyl diphosphate which is the chemical precursor to the monoterpenes. Examples of monoterpenes having anti-cancer properties are limonene, perillyl alcohol and geraniol, as discussed supra. Examples of nucleic acid sequences that encode monoterpene synthases are disclosed in the following, copending patent applications, each of which is incorporated herein by reference: U.S. patent application Ser. No. 08/846,526 "DNA Encoding Limonene Synthase from Mentha spicata"; U.S. patent application Ser. No. 08/937,540 "Monoterpene Synthases from Common Sage (Salvia officinalis) and PCT Patent Application Serial Number PCT/US98/14528 "Monoterpene Synthases from Grand fir (Abies grandis)."

Several methods are known in the art for the introduction of genes into human cells. For example, cell-based therapy can be used to introduce genes into cells while they are outside of the body. Cell-based approaches involve removing cells from a patient, introducing genes encoding a therapeutic protein into the removed cells, and returning the cells to the patient by cell transplantation or transfusion. The cell-based approach has been used to treat Severe Combined Immune Deficiency (SCID), which is due to inherited defects in the enzyme adenosine deaminase (ADA). The gene therapy treatment of SCID involved removal of peripheral blood lymphocytes or bone marrow progenitor cells from affected individuals, introduction of the normal ADA gene into the chromosomes of these cells using retroviral vectors, and reintroduction of the genetically engineered cells to the patient (C. Bordignon et al. Science 270:470, 474 (1995), R. M. Blaese et al., Science 270:475–479 (1995); D. B. Kohn et al., Nature Med 1:1017–1023 (1995)). Initial results demonstrated that the genetically engineered cells will persist for prolonged periods of time, and that low level expression of ADA can be established.

Analogous cell-based approaches have been used to treat familial hypercholesterolemia (LDL-receptor deficiency) (M. Grossman et al., Nature Genetics 6:335 41 (1994); M. Grossman et al., Nature Med 1:1148–1154 (1995)) and Gaucher disease (J. A. Nolta et al., J. Clin. Invest. 90:342–348 (1992); L. Xu et al., Exptl. Hematol. 22:223–230 (1994); T. Ohashi et al., Proc. Natl. Acad. Sci. USA. 89:11332–11336 (1992)).

Genes can be introduced into cells in situ, or after removal of the cells from the body, by means of viral vectors. For example, retroviruses are RNA viruses that have the ability to insert their genes into host cell chromosomes after infection. Retroviral vectors have been developed that lack the genes encoding viral proteins, but retain the ability to infect cells and insert their genes into the chromosomes of the target cell (A. D. Miller, Hum. Gen. Ther. 1:5–14 (1990)). Retroviruses will only efficiently infect dividing cells, thus when retroviruses are used to introduce genes into cells that have been removed from the body, cell division is stimulated with growth-promoting media or specific factors. In vivo application of retroviruses has been achieved by administration of virus-producing cells directly into tumors. Virus particle released by the infected cell will infect adjacent tumor cells, hence only a relatively small percentage of cells in a tumor need be initially infected in order to ultimately introduce the targeted gene into most or all of the tumor cells. (K. W. Culver et al., Science 256:1550–1552 (1992)).

Adenoviral vectors are designed to be administered directly to patients. Unlike retroviral vectors, adenoviral vectors do not integrate into the chromosome of the host cell. Instead, genes introduced into cells using adenoviral vectors are maintained in the nucleus as an extrachromosomal element (episome) that persists for a limited time period. Adenoviral vectors will infect dividing and non-dividing cells in many different tissues in vivo including airway epithelial cells, endothelial cells, hepatocytes and various tumors (B. C. Trapnell, Adv Drug Del Rev. 12:185–199 (1993)).

Another viral vector is the herpes simplex virus, a large, double-stranded DNA virus that has been used in some initial applications to deliver therapeutic genes to neurons and could potentially be used to deliver therapeutic genes to some forms of brain cancer (D. S. Latchman, Mol. Biotechnol. 2:179–95 (1994)). Recombinant forms of the vaccinia virus can accommodate large inserts and are generated by homologous recombination. To date, this vector has been used to deliver interleukins (ILs), such as human IL-1β and the costimulatory molecules B7-1 and B7-2 (G. R. Peplinski et al., *Ann. Surg. Oncol.* 2:151–9 (1995); J. W. Hodge et al., *Cancer Res.* 54:5552–55 (1994)).

Another approach to gene therapy involves the direct introduction of DNA plasmids into patients. (F. D. Ledley, *Hum. Gene Ther.* 6:1129–1144 (1995)). The plasmid DNA is taken up by cells within the body and can direct expression of recombinant proteins. Typically plasmid DNA is delivered to cells in the form of liposomes in which the DNA is associated with one or more lipids, such as DOTMA (1,2,-diolcyloxypropyl-3-trimethyl ammonium bromide) and DOPE (dioleoylphosphatidylethanolamine). Formulations with DOTMA have been shown to provide expression in pulmonary epithelial cells in animal models (K. L. Brigham et al., *Am. J Med Sci*, 298:278–281 (1989); A. B. Canonico et al., *Am. J Respir. Cell. Mol. Biol.* 10:24–29 (1994)). Additionally, studies have demonstrated that intramuscular injection of plasmid DNA formulated with 5% PVP (50,000 kDa) increases the level of reporter gene expression in muscle as much as 200-fold over the levels found with injection of DNA in saline alone (R. J. Mumper et al., *Pharm. Res.* 13:701–709 (1996); R. J. Mumper et al., *Proc. Intern. Symp. Cont. Rol. Bioac. Mater.* 22:325–326 (1995)). Intramuscular administration of plasmid DNA results in gene expression that lasts for many months (J.A. Wolff et al., *Hum. Mol. Genet.* 1:363–369 (1992); M. Manthorpe et al., *Hum. Gene Ther.* 4:419–431 (1993); G. Ascadi etal., *New Biol.* 3:71–81 (1991), D. Gal et al., *Lab. Invest.* 68:18–25 (1993)).

Additionally, uptake and expression of DNA has also been observed after direct injection of plasmid into the thyroid (M. Sikes et al., *Hum. Gene Ther.* 5:837–844 (1994)) and synovium (J. Yovandich et al., *Hum. Gene Ther.* 6:603–610 (1995)). Lower levels of gene expression have been observed after interstitial injection into liver (M. A. Hickman et al., *Hum. Gene Ther.* 5:1477–1483 (1994)), skin (E. Raz et al., *Proc. Natl. Acad. Sci.* 91:9519–9523 (1994)), instillation into the airways (K. B. Meyer et al., *Gene Therapy* 2:450–460 (1995)), application to the endothelium (G. D. Chapman et al., *Circulation Res.* 71:27–33 (1992); R. Riessen et al., *Human Gene Therapy*, 4:749–758 (1993)), and after intravenous administration (R. M. Conry et al., *Cancer Res.* 54:1164–1168 (1994)).

Various devices have been developed for enhancing the availability of DNA to the target cell. A simple approach is to contact the target cell physically with catheters or implantable materials containing DNA (G. D. Chapman et al., *Circulation Res.* 71:27–33 (1992)). Another approach is to utilize needle-free, jet injection devices which project a column of liquid directly into the target tissue under high pressure. (P. A. Furth et al., *Anal Biochem.* 20:365–368 (1992); (H. L. Vahlsing et al., *J. Immunol. Meth.* 175:11–22 (1994); (F. D. Ledley et al., *Cell Biochem.* 18A:226 (1994)).

Another device for gene delivery is the "gene gun" or Biolistic™, a ballistic device that projects DNA-coated micro-particles directly into the nucleus of cells in vivo. Once within the nucleus, the DNA dissolves from the gold or tungsten microparticle and can be expressed by the target cell. This method has been used effectively to transfer genes directly into the skin, liver and muscle (N. S. Yang et al., *Proc. Natl. Acad. Sci.* 87:9568–9572 (1990); L. Cheng et al., *Proc. Natl. Acad. Sci. USA.* 90:4455–4459 (1993); R. S. Williams et al., *Proc. Natl. Acad. Sci.* 88:2726–2730 (1991)).

Another approach to targeted gene delivery is the use of molecular conjugates, which consist of protein or synthetic ligands to which a nucleic acid- or DNA-binding agent has been attached for the specific targeting of nucleic acids to cells (R. J. Cristiano et al., *Proc. Natl. Acad. Sci. USA* 90:11548–52 (1993); B. A. Bunnell et al., *Somat. Call Mol. Genet.* 18:559–69 (1992); M. Cotten et al., *Proc. Natl. Acad. Sci. USA* 89:6094–98 (1992)). Once the DNA is coupled to the molecular conjugate, a protein-DNA complex results. This gene delivery system has been shown to be capable of targeted delivery to many cell types through the use of different ligands (R. J. Cristiano et al., *Proc. Natl. Acad. Sci. USA* 90:11548–52 (1993)). For example, the vitamin folate has been used as a ligand to promote delivery of plasmid DNA into cells that overexpress the folate receptor (e.g., ovarian carcinoma cells) (S. Gottschalk et al., *Gene Ther.* 1:185–91 (1994)). The malaria circumsporozoite protein has been used for the liver-specific delivery of genes under conditions in which ASOR receptor expression on hepatocytes is low, such as in cirrhosis, diabetes, and hepatocellular carcinoma (Z. Ding et al., *J. Biol. Chem.* 270:3667–76 (1995)). The overexpression of receptors for epidermal growth factor (EGF) on cancer cells has allowed for specific uptake of EGF/DNA complexes by lung cancer cells (R. Cristiano et al., *Cancer Gene Ther.* 3:4–10 (1996)).

Targeted expression of genes encoding proteins having anti-cancer activity can be achieved by placing the transgene under the control of an inducible promoter. For example, the promoter for the carcinoembryonic antigen (CEA) gene has been incorporated in vectors and it has directed cell-specific expression of the resulting CEA-expression vector constructs in tumors cells, such as those of pancreatic carcinoma (J. M. DiMaio et al., *Surgery* 116:205–13 (1994)). The regulatory sequences of the human surfactant protein A gene have been used to generate cell-specific expression in non-small-cell lung cancers that express this protein (M. J. Smith et al., *Hum. Gene Ther.* 5:29–35 (1994)).

Another approach to introducing geranyl diphosphate synthase protein (large and small subunits), and monoterpene synthase protein, into a cancerous cell is to directly introduce the purified protein into the body. Typically, the protein is introduced in association with another molecule, such as a lipid, to protect the protein from enzymatic degradation. For example, the covalent attachment of polymers, especially polyethylene glycol (PEG), has been used to protect certain proteins from enzymatic hydrolysis in the body and thus prolong half-life (F. Fuertges, et al., *J. Controlled Release*, 11:139 (1990)). Many polymer systems have been reported for protein delivery (Y. H. Bae, et al.,*J. Controlled Release*, 9:271 (1989); R. Hori, et al., *Pharm. Res.*, 6:813 (1989); I. Yamakawa, et al., *J. Pharm. Sci.*, 79:505 (1990); I. Yoshihiro, et al., *J. Controlled Release*, 10:195 (1989); M. Asano, et al., *J. Controlled Release*, 9:111 (1989); J. Rosenblatt et al., *J. Controlled Release*, 9:195 (1989); K. Makino, *J.Controlled Release*, 12:235 (1990); Y. Takakura et al.,*J.Pharm. Sci.*, 78:117 (1989); Y. Takakura et al., *J.Pharm. Sci.*, 78:219 (1989)).

Therapeutic proteins can be introduced into the body by application to a bodily membrane capable of absorbing the protein, for example the nasal, gastrointestinal and rectal membranes. The protein is typically applied to the absorptive membrane in conjunction with a permeation enhancer. (V. H. L. Lee, *Crit. Rev. Ther. Drug Carrier Syst.*, 5:69 (1988); V. H. L. Lee, *J.Controlled Release*, 13:213 (1990); V. H. L. Lee, Ed., *Peptide and Protein Drug Delivery*, Marcel Dekker, New York (1991); A. G. DeBoer et al., *J.Controlled Release*, 13:241 (1990)). For example, STDHF is a synthetic derivative of fusidic acid, a steroidal surfactant that is similar in structure to the bile salts, and has been used as a permeation enhancer for nasal delivery. (W. A. Lee, *Biopharm.* Nov./Dec., 22, 1990).

Additionally, microspheres bearing therapeutic protein can be delivered to the body. In one application, a bioadhesive was used to hold microspheres bearing protein in place in the nasal passages. When an absorption enhancer was incorporated into the microsphere with the protein, bioavailability was increased (L. Illum, et al., *Int. J. Pharm.*, 63:207 (1990); N. F. Farraj et al., *J. Controlled Release*, 13:253 (1990)).

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 (1982)), and Goeddel et al. (*Nucleic Acids Res.*, supra).

The following examples merely illustrate the best mode now contemplated for practicing the invention, but should not be construed to limit the invention.

EXAMPLES

Example 1

Isolation of Geranyl Diphosphate Synthase Large Subunit

Plant materials, substrates and reagents. Mint plants (*Mentha spicata* and *M x piperita*) were propagated and grown as previously described (W. Alonso et al., *J. Biol. Chem.* 267:7582–7587, 1992). Newly emerged, rapidly expanding leaves (5–10 mm long) of vegetative stems (3–7 weeks-old) were used for the preparation of glandular trichome cells for enzyme purification (J. Gershenzon et al., *Anal. Biochem.* 200:130–138, 1992). [4-$^{14}$C]Isopentenyl diphosphate (54 Ci/mol) was purchased from DuPont/NEN. Dimethylallyl diphosphate was synthesized as described (V. J. Davisson et al., *Methods Enzymol.* 110:130–144, 1985), as was geranyl diphosphate (R. Croteau et al., *Arch. Biochem. Biophys.* 309:184–192, 1994) and farnesyl diphosphate (V. M. Dixit et al., *J. Org Chem.* 46:1967–1969, 1981).

Assay for prenyltransferase activity. To 10 μl of enzyme solution was added 70 μl Mopso buffer (25 mM, pH 7.0) containing 10% glycerol, 10 mM MgCl$_2$, and 1 mM DTT. DMAPP (50 μM) and [4-$^{14}$C]IPP (7 μM) were added (100 μl total volume) to initiate the reaction, and the contents were overlaid with 1 ml hexane. The mixture was vortexed briefly and then incubated for 1 h at 31° C. After incubation, 10 μl of 3 N HCl was added, the contents vortexed and centrifuged, and hydrolysis of the products was continued for 20 min at 31° C. After acid hydrolysis was complete, the reaction mixture was again vortexed and centrifuged so that the products derived from the acid labile allylic diphosphates (or those alcohols derived from hydrolysis by endogenous phosphatases) were partitioned into the hexane layer. The hexane was removed and the radioactive products contained therein were measured by liquid scintillation counting of an aliquot. For the assay based on enzymatic, rather than acid, hydrolysis, the diphosphate ester products and remaining substrates of the incubation mixture were hydrolyzed by treatment with 1 unit each (2 mg) of wheat germ alkaline phosphatase and potato apyrase, added to each assay in a volume of 1 ml of 200 mM Tris buffer (pH 9.5), and allowed to incubate for at least 8 h at 30° C. The organic extract was then isolated for analysis as before.

Product identification. For the identification of reaction products, 50 μl of the enzyme preparation was diluted into 130 μl of Mopso buffer (25 mM, pH 7.0) containing 10% glycerol, 10 mM MgCl$_2$, and 1 mM DTT. DMAPP, GPP or FPP (35 μM) and [4-$^{14}$C]IPP (35 μM) were added to initiate the reaction for GPP synthase, FPP synthase and GGPP synthase, respectively, and pentane was substituted for the hexane overlay to improve recovery. After acid or enzymatic hydrolysis and removal of the pentane layer as described above, the reaction mixture was extracted with 2×1 ml of diethyl ether to ensure complete recovery of products. The combined organic extract was then dried over anhydrous Na$_2$SO$_4$ and concentrated to 100 μl, followed by the addition of internal standards and further concentration to 20 μl for radio-GLC analysis. The products sought were: from geranylgeranyl diphosphate, all trans-geranylgeraniol from enzyme (phosphatase)-catalyzed hydrolysis in addition to geranylnerol and geranyllinalool from acid catalyzed rearrangement (total C$_{20}$ alcohols); from farnesyl diphosphate, all trans-farnesol from phosphatase-catalyzed or acid hydrolysis, and cis, trans-farnesol and nerolidol from acid-catalyzed rearrangement (total C$_{15}$ alcohols); from geranyl diphosphate, geraniol from phosphatase-catalyzed or acid hydrolysis, and nerol and linalool from acid-catalyzed rearrangement (total C$_{10}$ alcohols); and total C$_5$ alcohols (dimethylallyl alcohol, isopentenol and dimethylvinyl carbinol).

Preparation of mint glandular trichome extracts. Glandular trichome cell clusters (approximately 2×10$^7$) were isolated from 40 g of leaf tissue following procedures previously described (J. Gershenzon et al., *Anal. Biochem.* 200:130–138, 1992). The isolated cell clusters were suspended in potassium phosphate buffer (50 ml, 100 mM, pH 7.4, containing 5 g XAD, 0.5 g PVPP, 250 mM sucrose, 1 mM DTT, 1 mM Benzamidine and 1 mM Na$_4$EDTA) and disrupted by sonication (Braun-sonic 2000, full power, five 15 s bursts separated by 45 s cooling in ice). The sonicate was filtered through a 20 μm nylon mesh and the filtrate was brought to 100 ml by the addition of 50 ml potassium phosphate buffer without XAD or PVPP. The sonicate was then centrifuged at 12.000g (30 min), then at 195,000g (90 min), and the supernatant was utilized as the enzyme source.

Dye-ligand interaction chromatography. The supernatant (generally combined from two gland preparations, ~200 ml) was dialyzed (2×4° C., 18 h total) in MES buffer (4 liters, 25 mM, pH 6.2) containing 10% glycerol, 1 mM DTT, and 10 MM MgCl$_2$. The dialyzed supernatant was equally divided into 8 (50 ml) polypropylene tubes containing 5 ml of DyeMatrex Red A Gel (Amicon) equilibrated with dialysis buffer in each tube. After 1 h of gentle mixing (Labquake), the contents were poured into eight 1.5×12 cm polypropylene columns (Bio-Rad), gravity drained, and washed with 4× volumes of dialysis buffer. Geranyl diphosphate synthase was then eluted with Hepes buffer (240 ml, 25 mM, pH 7.2) containing 10% glycerol, 5 mM potassium phosphate, 1 mM DTT, and 1 mM EDTA. The entire procedure was performed at 0–4° C.

Anion exchange chromatography. The elutant from the dye-ligand interaction chromatography step was loaded on to an HR 10/10 column containing Source 15Q anion-exchange media (Pharmacia Biotech) equilibrated in Hepes buffer (25 mM, pH 7.5) containing 10% glycerol, 10 mM $MgCl_2$ and 1 mM DTT. Geranyl diphosphate synthase was eluted with a discontinuous gradient (0–90 and then 90–370 mM KCl; total volume 140 ml). Farnesyl diphosphate synthase activity eluted at 90 mM KCl; geranyl diphosphate synthase activity eluted at ~200 mM KCl; geranylgeranyl diphosphate synthase activity was not detected in any fraction of the chromatographic run, including the flowthrough upon sample loading and the final 1 M KCl wash step. This anion-exchange chromatography step afforded the most efficient purification of geranyl diphosphate synthase, and the fractions (6 ml) with the highest activity were collected and stored at ~80° C.

To identify the geranyl diphosphate synthase protein in the anion-exchange chromatography fractions, equal volumes from each fraction containing geranyl diphosphate synthase activity were individually loaded onto separate lanes of an SDS-PAGE gel, and the proteins contained therein were resolved and silver stained to reveal the presence of three prominent proteins, at 28±1 kDa, 31±1 kDa and 37±1 kDa, which best tracked the activity. The protein at 28±1 kDa was initially considered to represent the geranyl diphosphate synthase based on staining intensity, coincidence of protein and activity, and consistency of size of this presumptive subunit of an assumed homodimer of ~60 kDa. The size of the native enzyme from Mentha (70±7 kDa) was initially established by gel permeation chromatography (Superdex 75), and all previously reported short-chain prenyltransferases are homodimers (K. Ogura and T. Koyama, *Chem. Rev.* 98:1263–1276, 1998; T. Koyama and K. Ogura, "Isopentenyl Diphosphate Isomerase and Prenyltransferases," in Comprehensive Natural Products Chemistry: Isoprenoids, D. E. Cane, ed., Vol. 2, Elsevier Science, Oxford, 1999, pp. 69–96).

Preparative SDS-PAGE. The partially purified geranyl diphosphate synthase from the anion exchange chromatography step (60 ml) was heated to 95° C. for 15 min, cooled, and exhaustively dialyzed in distilled water (2×4 liters, 18 h, 4° C.). The protein solution was then lyophilized, and the dried powder was suspended in 100 μl of SDS buffer plus 50 μl of 3× loading buffer and separated by SDS-PAGE on 12.5% acrylamide at 35 mA for 6 h [15 cm×18 cm×1.5 mm gel]) by standard protocols (U. K. Laemmli, *Nature* 227:680–685, 1970). Coomassie Blue staining revealed at least ten protein bands, with prominent species corresponding to 28±1, 31±1 and 37±1 kDa that were estimated at ~10 μg protein based upon staining intensity calibrated with carbonic anhydrase as reference. All ten protein bands, including the 28 and 37 kDa gel bands that were the most coincident with geranyl diphosphate synthase activity on anion-exchange chromatography, were excised from the gel and stored in microcentrifuge tubes.

Protein sequencing. The excised gel bands containing the ten separated proteins were individually digested with trypsin (Promega V511/1,2) following published protocols (J. E. Coligan, "Digestion of Proteins in Gels for Sequence Analysis," in *Current Protocols in Protein Science*, Vol. 1, J. E. Coligan et al., eds., John Wiley and Sons, New York, 1996, pp. 11.3.1–11.3.13). The resulting peptide mixtures, including that derived from the 37 kDa presumptive geranyl diphosphate synthase large subunit, were then individually loaded onto a reversed phase HPLC (C18) column (Brownlee ODS-300), which was equilibrated with distilled water/1% TFA (buffer A) and developed by gradient elution with buffer B consisting of 70% $CH_3CN$, 29% distilled water and 1% TFA (0–60 min, 0%–37% buffer B/60–90 min, 37%–75% buffer B/90–105 min, 75%–100% buffer B). The purified peptides were subjected to amino-terminal sequence analysis via Edman degradation at the Washington State University Laboratory for Biotechnology and Bioanalysis. Two of the five purified peptides derived from the 28 kDa protein yielded unambiguous peptide sequences comprising FGLYQGTL (SEQ ID NO:12) and VIIEIS (SEQ ID NO:13), thereby confirming that the 28 kDa protein is the protein characterized as geranyl diphosphate synthase in U.S. Pat. No. 5,876,094 to Croteau et al. Four of the six purified peptides derived from the 37 kDa protein yielded sequences comprising LIGVE (peptide 1) (SEQ ID NO:3), YIAYR (peptide 2) (SEQ ID NO:4), TAALLTGSVVLGAIL (peptide 3) (SEQ ID NO:5) and EAVETLLHF (peptide 4) (SEQ ID NO:6). No other useful amino acid sequence information was obtained from the remaining peptides derived from the 28 kDa protein or the 37 kDa protein because of ambiguities due to low recoveries of the peptide or the presence of contaminants.

Example 2

Cloning of Geranyl Diphosphate Synthase Large Subunit cDNAs

Since further scale-up of the geranyl diphosphate synthase large subunit purification protocol was impractical, and because the limited peptide sequence information, due to degeneracy considerations, precluded a reverse genetic approach to cDNA cloning, alternate means to acquire a geranyl diphosphate synthase large subunit cDNA were attempted. To improve the chances for acquiring this cDNA target, methods were developed to isolate mRNA specifically from mint oil glands, the exclusive site of monoterpene biosynthesis in Mentha (J. Gershenzon et al., *Anal. Biochem.* 200:130–138, 1992), for the purpose of constructing a highly enriched cDNA library containing the sequences of interest.

Glandular trichome cDNA library construction. Available methods of RNA isolation and purification, and for secretory cell isolation, are incompatible. The use of chaotropic salts or organic solvents as an initial denaturant of ubiquitous RNases is not possible because of the long leaf imbibition periods required during the initial stages of secretory cell isolation. A modified RNA isolation and purification protocol was successfully developed which incorporated the use of low molecular weight RNase inhibitors in the imbibition medium. Thus, secretory cells were isolated from 5-day-old peppermint (J. Gershenzon et al., *Anal. Biochem.* 200:130–138, 1992) from plants which had been grown as previously described (W. R. Alonso et al., *J. Biol. Chem.* 267:7582–7587, 1992) but, in this case using 5 mM aurintricarboxylic acid (R. G. Gonzalez et al., *Biochemistry* 19:4299–4303, 1980) and 1 mM thiourea (E. Van Driessche et al., *Anal. Biochem.* 141:184–188, 1984) throughout all procedures to prevent enzymatic and nonenzymatic degradation of RNA.

Total RNA was then extracted from the isolated secretory cells using the method of Logemann (J. Logemann et al., *Anal. Biochem.* 163:16–20, 1987) which had been modified (S. Lupien et al., *Arch. Biochem. Biophys.* 368: 181–192, 1999) to include a 10% ethanol precipitation step to remove interfering polysaccharides. Poly(A)⁺-RNA was purified by chromatography on oligo(dT)-cellulose (Pharmacia), and 5 µg of the resulting mRNA was utilized to construct a λZAPII cDNA library according to the manufacturer's instructions (Stratagene).

Homology-based cloning attempts. Concurrent with attempts to purify and sequence the native geranyl diphosphate synthase protein, a homology-based PCR strategy was devised to isolate the target cDNA, based on the assumption that geranyl diphosphate (GPP) synthase would resemble in sequence farnesyl diphosphate (FPP) synthase and/or geranylgeranyl diphosphate (GGPP) synthase. After over a year of effort and sequencing of numerous candidate PCR products, the only relevant amplicons obtained showed very high homology to farnesyl diphosphate synthase. Subsequent library screening with these amplicons as labeled probes led to the acquisition of the corresponding full-length cDNA, that when functionally expressed in E. coli confirmed that this cDNA did, in fact, encode FPP synthase.

Random sequencing of an oil gland library. Random cDNA clones from a peppermint oil gland cDNA library were sequenced in an effort to identify prenyltransferase (GPP synthase)-like cDNAs. Plasmids were purified from individual colonies arising from a mass excision of mint gland λZAPII phagemids (Stratagene) and the inserts were sequenced (DyeDeoxy Terminator Cycle Sequencing, applied Biosystems), with the data subsequently acquired on the ABI sequenator. The NCBI BLAST server was used for database searching using the programs of the GCG Wisconsin package (Genetics Computer Group, *Program Manual for the Wisconsin Package*, Version 8, Genetics Computer Group, Madison, Wis, 1994).

Of the approximately 130 individual clones initially isolated and sequenced, one (SEQ ID NO:1) revealed significant homology to geranylgeranyl diphosphate (GGPP) synthases of plant origin (74–93% similarity; 67–83% identity). Two primers designated GG23F (SEQ ID NO:7) and GG23R (SEQ ID NO:8) were designed to amplify a 5'-region (101 bp) of this sequence (SEQ ID NO:9). The resulting amplicon was then labeled with [³²P]dATP using the same primers (SEQ ID NO:7) (SEQ ID NO:8), and employed as a hybridization probe to screen at high stringency the oil gland cDNA library. Ten positive clones were purified through a second round of screening and were sequenced to yield the full-length cDNA insert of pMp23.10 (SEQ ID NO:1). In spite of the fact that geranylgeranyl diphosphate synthase activity could not be demonstrated in mint oil gland extracts, this clone (SEQ ID NO:1) was initially considered to encode geranylgeranyl diphosphate synthase since all plants are required to produce geranylgeranyl diphosphate as an essential precursor of chlorophyll, carotenoids, and gibberellin plant growth hormones (C. A. West, "Biosynthesis of Diterpenes," in *Biosynthesis of Isoprenoid Compounds*, J. W. Porter and S. L. Spurgeon, eds., Vol 1, Wiley, New York, N.Y., 1981, pp. 375–411).

As disclosed in Example 1 herein, purification of the native geranyl diphosphate synthase large subunit from mint yielded a 37 kDa protein upon SDS-PAGE. Significantly, alignment of the four peptide sequences derived from this 37 kDa protein observed in the highly purified preparation, with the deduced amino acid sequence of the protein encoded by the insert of pMp23.10 (SEQ ID NO:1), revealed that peptide 1 (LIGVE) (SEQ ID NO:3) corresponded exactly to deduced amino acid residues 333 to 337 of SEQ ID NO:2, that peptide 2 (YIAYR) (SEQ ID NO:4) corresponded exactly to deduced amino acid residues 371 to 375 of SEQ ID NO:2, that peptide 3 (TAALLTGSVVLGAIL) (SEQ ID NO:5) corresponded to residues 263 to 277 of SEQ ID NO:2 and peptide 4 (EAVETLLHF) (SEQ ID NO:6) to residues 349–357 of the pMp23.10 protein (SEQ ID NO:2). This observation cast some doubt upon the identification of the pMp23.10 protein (SEQ ID NO:2) as a geranylgeranyl diphosphate synthase (for which no activity was observed), and prompted further evaluation of this clone.

Subcloning and heterologous expression. The cDNAs were subcloned into expression vectors that would allow high levels of bacterial (E. coli) production, as well as the ability to co-express both clones in a single bacterial cell. Plants employ different codon usage than E. coli, and the presence of the arginine codons AGA and AGG in a sequence can lead to mistranslation or truncation of such eukaryotic encoded proteins when heterologously expressed in E. coli. Since most of the arginines in the sequences of clones Mp13.18 (SEQ ID NO:11) (small subunit) and Mp23.10 (SEQ ID NO:2) (large subunit) are coded for usage by these rare E. coli tRNAs, the pET3a/pACYC-derived vector, pSBETa, was used. This vector encodes kanamycin resistance, drives expression with T7 DNA polymerase from the strong T7 promoter, and additionally carries the argU gene for the tRNA that specifies rare codon usage to improve translation of such arginine residues (P. M. Schenk et al., *BioTechniques* 19:196–200, 1995).

The full-length open reading frame of pMp13.18 (SEQ ID NO:10) was cloned directionally into pSBETa by the addition of an NdeI site at the starting methionine by site directed mutagenesis (QuickChange, Stratagene), and the use of a convenient BamHI site (8 bp downstream of the stop codon). The vector and the engineered derivative of pMp13.18 (SEQ ID NO:10), designated pMp13.18N, were doubly-digested with BamHI and NdeI, the fragment purified and ligated overnight, and then transformed into E. coli XL1-Blue competent cells. The resulting plasmid, designated pSB13.18, was purified, sequenced to verify that no undesired changes occurred during mutagenesis, and then transformed into the T7 expression strain E. coli BLR(DE3). Construction of a series of clones in which the plastidial transit peptide was truncated at different positions was performed similarly, with the incorporation of the NdeI site, and thus the starting methionine, at positions 31, 42, 48, 50, 55, and 63. The resulting plasmids are designated as pSB13.18M31, pSB13.18M42, etc., to indicate the position of truncation and of the new starting methionine.

The full-length clone pMp23.10 (SEQ ID NO:1), acquired as above, was also modified by site directed mutagenesis as above to install both a 5'-NdeI site and a 3'-BamHI site beyond the stop codon, thereby creating pMp23.10NB, which was doubly-digested and ligated into pSBET, and designated pSB23.10. Sequencing revealed that no errors were introduced during mutagenesis. For co-expression studies, the full-length open reading frame of pMp23.10 (SEQ ID NO:1) and a truncation of the leader sequence were subcloned into the ampicillin resistance-encoding vector pET32a (Novagen) which had been digested with NdeI and BamHI and gel purified (yielding essentially pET3a with a T7lac promoter). The full-length clone (pMp23.10NB) was similarly double-digested and gel purified, then ligated into pET32a to yield pET23.10. The truncation of the plastidial transit peptide was created by adding a BamHI overhang downstream of the stop codon and a 5'-NdeI overhang (and thus the starting methionine) at residue 83 using sticky-end PCR (K. Pham et al., *Biotechniques* 25:206–208, 1998), thereby yielding pET23.10M83. For expression of clone pET23.10 alone, this plasmid was co-transformed with pSBETa to take advantage of the ArgU gene of the latter. The above plasmids, as well as control pSBET and control pET plasmids (without insert), were transformed into *E. coli* BLR(DE3) for expression. For coexpression, *E. coli* BLR (DE3) was doubly transformed with pSB13.18 and pET23.10 (with dual antibiotic selection) to give pSB13.18-pET23.10/BLR.

Each transformant was grown at 37° C. in 1 L of LB medium (supplemented with 1% glucose) with kanamycin selection (for pSBET) or ampicillin selection (for pET), or with dual antibiotic selection (for co-expression using both plasmids), to $A_{600}$,=0.5. The transformed bacteria were then induced with 1 mM IPTG and allowed to express for 24 h at 15° C. The bacteria were harvested by centrifugation, washed once with Tris buffer (pH 7.0) containing 50 mM KCl, and resuspended in 25 ml sonication buffer (25 mM Hepes, pH 7.2, 10 mM $MgCl_2$, 10% glycerol, 1 mM DTT, 1 mM EDTA and 1 mM benzamidine) and disrupted by brief sonication (VirSonic, 25% power, two 30 s bursts, 0–4° C.). The sonicate was centrifuged at 12,000g (30 min), then at 195,000g (90 min). The supernatant (soluble enzyme fraction) was loaded onto an HR 5/5 column containing Source 15Q anion-exchange separation medium (Pharmacia Biotech) that had been equilibrated with Hepes buffer (25 mM, pH 7.5) containing 10% glycerol, 10 mM $MgCl_2$, 1 mM DTT and 1 mM benzamidine. A step gradient of KCl (0–85 mM (10 ml); 85 mM (15 ml); 85–600 mM (20 ml)) was applied, and 2 ml fractions were collected and assayed for prenyltransferase activity using $[^{14}C]$IPP and DMAPP (or GPP or FPP) as cosubstrates as described above.

Evaluation of the functional expression of recombinant geranyl diphosphate synthase, and other prenyltransferases, is compromised by the fact that host cells contain competing phosphatases that can hydrolyze both DMAPP and IPP cosubstrates, as well as the product of the reaction. Host cells also contain endogenous farnesyl diphosphate synthase, capable of converting DMAPP or GPP, plus IPP, to FPP; this enzyme is thus capable of depleting GPP formed by a recombinant synthase. Finally, the co-substrate DMAPP, at high concentration, can displace bound GPP as an intermediate of FPP and GGPP syntheses, leading to false positive indication of the presence of GPP synthase. For these reasons, partial purification of the recombinant proteins by anion-exchange chromatography is required to separate competing activities (*E. coli* farnesyl diphosphate synthase elutes at ~85 mM KCl; mint recombinant geranyl diphosphate synthase elutes free of competing activities at >90 mM KCl under these conditions), and empty vector controls are essential. Furthermore, the assay for recombinant prenyltransferase was designed, from studies with the native GPP synthase, to minimize false positives due to co-substrate effects and to incorporate appropriate controls (with boiled enzyme, no cofactor, etc.) for monitoring activity.

Confirmation of identity of geranyl diphosphate synthase clones. All constructs harboring clone Mp13.18 (SEQ ID NO:10) and its truncations (pSB13.18/BLR, pSB13.18M31/BLR, pSB13.18M42/BLR, pSB13.18M48/BLR, etc.) expressed prenyltransferase activity in crude cell-free extracts at a level that correspond to that of the pSBET (empty vector) controls, suggesting the presence of little or no prenyltransferase activity above endogenous levels present in the host. Separation of proteins in these extracts by anion-exchange chromatography revealed that essentially all of the prenyltransferase activity eluted at 85 mM KCl, coincident with host-derived farnesyl diphosphate synthase.

This assignment of the activity to *E. coli* farnesyl diphosphate synthase was confirmed by radio-gas chromatographic analysis of the $C_{15}$ products. Occasionally, very low levels of prenyltransferase activity was observed in the recombinant protein extracts, derived from several of the constructs, that eluted from the ion-exchange column at >90 mM KCl and this activity was confirmed to be geranyl diphosphate synthase by radio-gas chromatographic analysis of the $C_{10}$ products. However, expression of this activity was always low, and often inconsistent, and in this regard the truncations were no better than the full-length preprotein expressed from pSB 13.18/BLR.

The constructs harboring Mp23.10 (SEQ ID NO:1) and its truncation (pSB23.10/BLR, pET23.10/BLR and pET23.10M83/BLR) were also tested by functional expression and, as with clone Mp13.18 (SEQ ID NO:10), the expressed prenyltransferase activity in crude cell-free extracts of the transformed bacteria evidenced no significant difference from the empty vector controls, again suggesting the presence of little or no recombinant prenyltransferase activity above endogenous levels present in the host. Separation of proteins in these extracts by anion-exchange chromatography revealed that all of the prenyltransferase activity eluted at 85 mM KCL, coincident with host-derived farnesyl diphosphate synthase (confirmed by radio-gas chromatography). Thus, clone Mp23.10 (SEQ ID NO:1) did not express geranyl diphosphate synthase activity, farnesyl diphosphate synthase activity, or geranylgeranyl diphosphate synthase activity. Significantly, based on sequence comparison, clone Mp23.10 (SEQ ID NO:1) seemed to most closely resemble geranylgeranyl diphosphate synthases of plant origin, but this clone did not express a functional homodimeric geranylgeranyl diphosphate synthase, as might be expected based on literature precedent (K. Ogura and T. Koyama, *Chem. Rev.* 98:1263–1276, 1998; T. Koyama and K. Ogura, in *Comprehensive Natural Products Chemistry: Isoprenoids*, D. E. Cane, ed., Vol. 2, Elsevier Science, Oxford, 1999, pp. 69–96; K. Wang and S.-I. Ohnuma, *Trends Biochem.* Sci., in press).

Given the observation that the purified, native geranyl diphosphate synthase from mint yielded a 28 kDa protein and a 37 kDa protein upon SDS-PAGE, it seemed possible that clone Mp13.18 (SEQ ID NO:10) (encoding the 28 kDa protein) and clone Mp23.10 (SEQ ID NO:1) (encoding the 37 kDa protein) might represent the genes encoding the small and large subunits, respectively, of a heterodimeric geranyl diphosphate synthase. This suggestion, however, was inconsistent with the homodimeric nature of all short-chain prenyltransferases thus far reported (K. Ogura and T. Koyama, *Chem. Rev.* 98:1263–1276, 1998, T. Koyama and K. Ogura, "Isopentenyl Diphosphate Isomerase and Prenyltransferases," in *Comprehensive Natural Products Chemistry: Isoprenoids*, D. E. Cane, ed., Vol. 2, Elsevier Science, Oxford, 1999, pp. 69–96). Nevertheless, the possibility was examined by co-expression of clones Mp13.18 (SEQ ID NO:10) and Mp23.10 (SEQ ID NO:1) using the transformant pSB13.18-pET23.10/BLR. Cell-free extracts of the bacteria harboring both clones yielded levels of prenyltransferase activity significantly higher than the corresponding empty vector controls, and separation of activities by ion-exchange chromatography revealed the presence of a prenyltransferase that eluted at >90 mM KCL and that was absent in preparations from the controls. This new, recombinant prenyltransferase was confirmed to be geranyl diphosphate synthase by radio-gas chromatographic analysis demonstrating the exclusive production of the $C_{10}$ product. Since the conversion levels of the recombinant preparation approached those of the native enzyme under optimized assay conditions, it can be concluded that geranyl diphosphate synthase is a functional heterodimer comprised of a small subunit, such as that encoded by the cDNA insert of Mp13.18 (SEQ ID NO:10), and a large subunit, such as that encoded by the newly isolated cDNA insert of Mp23.10 (SEQ ID NO:1).

Size exclusion chromatography on a calibrated Sephacryl S-100 column revealed that the recombinant geranyl diphosphate synthase eluted as a single peak of activity at a volume corresponding to a molecular weight of 85,000±8,000, consistent with the formation of a functional heterodimer of the small and large subunits (i.e., 33.5 kDa plus 40.8 kDa of the respective subunit preproteins). Furthermore, SDS-PAGE of this partially purified material revealed the presence of essentially equimolar amounts of both subunits by silver staining and by calibrated immunoblotting with polyclonal antibodies independently raised in rabbits against each purified, denatured subunit, thus confirming the heterodimeric nature of this geranyl diphosphate synthase. Finally, a search of acquired random clones of the mint oil gland library for the large and small geranyl diphosphate synthase subunits, and their respective alleles, revealed abundances of 3/1200 (large subunit) and 4/1200 (small subunit) indicating comparable levels of the corresponding messages in the original pool and again supporting a 1:1 stoichiometry of the large and small subunits.

Example 3
Sequence Analysis and Related Considerations

The geranyl diphosphate synthase small subunit clone (SEQ ID NO:10) (1131 total nt), previously disclosed and characterized in U.S. patent Ser. No: 5,876,964 (which patent is expressly incorporated herein by reference in its entirety), encodes an open reading frame of 939 nucleotides, corresponding to a preprotein of 313 amino acids (SEQ ID NO:11) with a calculated molecular weight of 33,465. The first 48 deduced amino acid residues show the expected characteristics of an N-terminal plastidial targeting sequence (i.e., the sequence is rich in serine residues and amino acid residues with small, hydrophobic side chains, and is low in acidic residues (G. von Heijne et al., *Eur. J. Biochem.* 180:535–545, 1989)). The presence of such an amino-terminal targeting sequence is consistent with the plastidial origin of monoterpene biosynthesis in plant cells (M. L. Wise and R. Croteau, "Monoterpene Biosynthesis," in *Comprehensive Natural Products Chemistry: Isoprenoids*, D. E. Cane, ed., Vol. 2, Elsevier Science, Oxford, 1999, pp. 97–153), and with the localization of this enzyme exclusively within the plastids (E. Soler et al., Planta 187:171–175, 1992; G. Turner and R. Croteau, unpublished). By excluding the putative transit peptide of the preprotein, the amino acid sequence corresponds to a deduced mature, processed protein of molecular weight 28,485, in full agreement with a size of 28±1 kDa determined for this subunit of the native enzyme by SDS-PAGE.

The newly discovered geranyl diphosphate synthase large subunit clone (SEQ ID NO:1) (1341 total nt) encodes an open reading frame of 1131 nucleotides, corresponding to a preprotein of 377 amino acids (SEQ ID NO:2) with a calculated molecular weight of 40,800. The first 40 deduced amino acid residues show the expected characteristics of an N-terminal plastidial targeting sequence (ChloroP predictor, web server). By excluding the putative transit peptide in this case, the sequence corresponds to a deduced mature, processed protein of molecular weight of 36,400, in full agreement with a size of 37±1 kDa determined for this subunit of the native enzyme by SDS-PAGE. Given these considerations, the size of the functional heterodimer, following import, proteolytic processing and assembly in the plastids, would be predicted to be ~65 kDa (i.e., 28.5 kDa±36.4 kDa for the processed forms), which is consistent with a size of 70±7 kDa determined by gel permeation chromatography (on Superdex 75) of the native geranyl diphosphate synthase isolated from mint oil glands.

It is notable that the constituent sequences of the geranyl diphosphate ($C_{10}$) synthase more closely resemble those of plant-derived geranylgeranyl ($C_{20}$) diphosphate synthase than farnesyl ($C_{15}$) diphosphate synthase. Thus, the small subunit exhibits 26–30% identity and 54–56% similarity to GGPP synthase preproteins but only 17–18% identity and 37–42% similarity to FPP synthases. For the large subunit, the resemblance is more striking; 65–72% identity and 76–88% similarity to GGPP synthase preproteins but only 18–26% identity and 42–48% similarity to FPP synthases. These observations suggest the evolutionary origin of both GPP synthase subunits from GGPP synthase, which is also plastidial, not from FPP synthase, which is a cytosolic enzyme. Since it is clear from the expression studies that the large subunit, although it resembles GGPP synthase, is not a GGPP synthase, it is of interest to note that a GGPP synthase enzyme, or expressed gene, has not yet been verified to be present in mint oil glands, although it must be functional elsewhere in mint leaves for essential metabolic purposes.

Example 4
Characteristics of Presently Preferred Nucleic Acid Molecules that Encode Geranyl Diphosphate Synthase Small Subunit Proteins Presently preferred nucleic acid molecules that encode a geranyl diphosphate synthase small subunit protein useful in the practice of the present invention (for example, for coexpression with geranyl diphosphate synthase large subunit protein in a host cell) are capable of hybridizing to the nucleic acid sequence set forth in SEQ ID NO:10, or to the complementary sequence of the nucleic acid sequence set forth in SEQ ID NO:10, under the following stringent hybridization conditions: incubation in 5×SSC at 65° C. for 16 hours, followed by washing under the following conditions: two washes in 2×SSC at 18° C. to 25° C. for twenty minutes per wash, followed by one wash in 0.5×SSC at 55° C. for thirty minutes; most preferably, two washes in 2×SSC at 18° C. to 25° C. for fifteen minutes per wash, followed by two washes in 0.2×SSC at 65° C. for twenty minutes per wash.

The ability of presently preferred nucleic acid molecules that encode a geranyl diphosphate synthase small subunit protein to hybridize to the nucleic acid sequence set forth in SEQ ID NO:10, or to the complementary sequence of the nucleic acid sequence set forth in SEQ ID NO:10, can be determined utilizing the technique of hybridizing radiolabelled nucleic acid probes to nucleic acids immobilized on nitrocellulose filters or nylon membranes as set forth, for example, at pages 9.52 to 9.55 of Molecular Cloning, A Laboratory Manual (2nd edition), J. Sambrook, E. F. Fritsch and T. Maniatis eds, the cited pages of which are incorporated herein by reference.

The presently most preferred nucleic acid molecule encoding a geranyl diphosphate synthase small subunit protein is the nucleic acid molecule having the nucleic acid sequence set forth in SEQ ID NO:10.

Example 5
Characteristics of Presently Preferred Geranyl Diphosphate Synthase Small Subunit Proteins Presently preferred geranyl diphosphate synthase small subunit proteins useful in the practice of the present invention (for example, for coexpression with geranyl diphosphate synthase large subunit protein in a host cell) possess the properties set forth in Table 1 (geranyl diphosphate synthase small subunit is functional in the absence of geranyl diphosphate synthase large subunit, but at only about 1% of the activity level of the geranyl diphosphate synthase heterodimer). The presently most preferred geranyl diphosphate synthase small subunit protein has the amino acid sequence set forth in SEQ ID NO:11.

TABLE 1

Properties of Presently Preferred Geranyl Diphosphate Synthase Small Subunit Proteins

| | |
|---|---|
| Cofactor requirement: | Divalent metal ion (usually $Mg^{++}$ or $Mn^{++}$, potentially $Fe^{++}$, $Co^{++}$, $Zn^{++}$) |
| pH optimum: | from about pH 6.2 to about pH 7.8 |
| pI: | acidic, from about pH 4.5 to about pH 6.0 |
| $K_m$ (isopentenyl diphosphate): | <20 $\mu M$ |
| $K_m$ (dimethylallyl diphosphate): | <50 $\mu M$ |
| $K_m$ (metal ion): | $Mg^{++}$ <5 mM; $Mn^{++}$ <1 mM |
| $k_{cat}$: | <5/sec |
| Architecture: | Monomers or homodimers, with monomer molecular weight from about 30 kD to about 50 kD |
| Other properties: | Most are plastid-directed, operationally soluble, but relatively unstable enzymes. Highly specific for dimethylallyl diphosphate as allylic cosubstrate and for geranyl diphosphate as product (do not elongate beyond $C_{10}$). Inhibited by histidine- and arginine-directed reagents. |

Example 6
Characteristics of Presently Preferred Nucleic Acid Molecules that Encode Geranyl Diphosphate Synthase Large Subunit Proteins Presently preferred nucleic acid molecules that encode a geranyl diphosphate synthase large subunit protein useful in the practice of the present invention (for example, for coexpression with geranyl diphosphate synthase small subunit protein in a host cell) are capable of hybridizing to the nucleic acid sequence set forth in SEQ ID NO: 1, or to the complementary sequence of the nucleic acid sequence set forth in SEQ ID NO:1, under the following stringent hybridization conditions: incubation in 5×SSC at 65° C. for 16 hours, followed by washing under the following conditions: two washes in 2×SSC at 18° C. to 25° C. for twenty minutes per wash, followed by one wash in 1.0×SSC at 55° C. for thirty minutes, more preferably followed by two washes in 0.5×SSC at 65° C. for twenty minutes per wash.

The ability of presently preferred nucleic acid molecules that encode a geranyl diphosphate synthase large subunit protein to hybridize to the nucleic acid sequence set forth in SEQ ID NO:1, or to the complementary sequence of the nucleic acid sequence set forth in SEQ ID NO:1, can be determined utilizing the technique of hybridizing radiolabelled nucleic acid probes to nucleic acids immobilized on nitrocellulose filters or nylon membranes as set forth, for example, at pages 9.52 to 9.55 of Molecular Cloning, A Laboratory Manual (2nd edition), J. Sambrook, E. F. Fritsch and T. Maniatis eds, the cited pages of which are incorporated herein by reference.

Example 7
Characteristics of Presently Preferred Geranyl Diphosphate Synthase Large Subunit Proteins Presently preferred geranyl diphosphate synthase large subunit proteins useful in the practice of the present invention (for example, for coexpression with geranyl diphosphate synthase small subunit protein in a host cell) are capable of forming a functional heterodimer with geranyl diphosphate synthase small subunit protein. The resulting geranyl diphosphate synthase heterodimer is capable of catalyzing the condensation of dimethylallyl diphosphate (DMAPP) and isopentenyl diphosphate (IPP) to form geranyl diphosphate, and possesses the properties set forth in Table 2.

TABLE 2

Properties of Geranyl Diphosphate Synthase Heterodimers Including Presently Preferred Geranyl Diphosphate Synthase Large Subunit

| | |
|---|---|
| Cofactor requirement: | Divalent metal ion (usually $Mg^{++}$ or $Mn^{++}$, potentially $Fe^{++}$, $Co^{++}$, $Zn^{++}$) |
| pH optimum: | from about pH 6.2 to about pH 7.8 |
| pI: | acidic, from about pH 4.5 to about pH 6.0 |
| $K_m$ (isopentenyl diphosphate): | <20 $\mu M$ |
| $K_m$ (dimethylallyl diphosphate): | <50 $\mu M$ |
| $K_m$ (metal ion): | $Mg^{++}$ <5 mM; $Mn^{++}$ <1 mM |
| $k_{cat}$: | <5/sec |
| Architecture: | Native heterodimeric protein of 60–100 kD |
| Other properties: | Most are plastid-directed, operationally soluble, but relatively unstable enzymes. Highly specific for dimethylallyl diphosphate as allylic cosubstrate and for geranyl diphosphate as product (do not elongate beyond $C_{10}$). Inhibited by histidine- and arginine-directed reagents. |

Additionally, presently preferred geranyl diphosphate synthase large subunit proteins useful in the practice of the present invention are recognized by antibodies raised against the geranyl diphosphate synthase large subunit protein having the amino acid sequence disclosed in SEQ ID NO:2. Antibodies can be raised against geranyl diphosphate synthase large subunit protein by any art-recognized means. Methods for preparing monoclonal and polyclonal antibodies are well known to those of ordinary skill in the art and are set forth, for example, in chapters five and six of *Antibodies A Laboratory Manual*, E. Harlow and D. Lane, Cold Spring Harbor Laboratory (1988), the cited chapters of which are incorporated herein by reference. For example, polyclonal antibodies have been successfully raised against the geranyl diphosphate synthase large subunit protein having the amino acid sequence disclosed in SEQ ID NO:2 by first purifying this protein by anion exchange chromatography followed by excision of the Coomassie Blue-stained protein from an SDS-PAGE gel. About 1.5 mg of the geranyl diphosphate synthase large subunit protein having the amino acid sequence disclosed in SEQ ID NO:2 was excised from a Coomassie Blue-stained SDS-PAGE gel and used to inject two rabbits (100 $\mu g$ per injection). Antibodies were bled on the 7th and 9th week after injection.

Example 8
A PCR Strategy for Cloning Nucleic Acid Molecules Encoding Geranyl Diphosphate Synthase Large Subunit The following PCR strategy can be utilized to clone additional nucleic acid molecules (preferably cDNA molecules) of the present invention that encode a geranyl diphosphate synthase large subunit protein. The forward primer for the PCR reaction has the sequence: AAR CCM ACN AAY CAY ATG (SEQ ID NO:14) (corresponding to amino acids Lys[179] through Met[184] of SEQ ID NO:2). The reverse primer for the PCR reaction has the sequence: YC RTG NGG RTG RAA RTG (SEQ ID NO:15) (corresponding to amino acids Arg[361] through His[356] of SEQ ID NO:2). A 100 µl PCR reaction contains: 20mM Tris-HCl (pH8.4), 50 mM KCl, 3.5mM $MgCl_2$, 250µM of each DNTP, 0.1µM of each primer, 2.5 units of Taq DNA polymerase, and 1000 to 1,000,000 template molecules (such as cDNA molecules). Representative temperature cycling conditions are: 35 cycles, each cycle including 1 min at 94° C. to denature, 1 min at 50° C. to anneal, 1 min at 72° C. to extend.

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. An isolated nucleic acid molecule encoding a geranyl diphosphate synthase large subunit protein, said nucleic acid molecules hybridizing to the complement of a nucleic acid molecule consisting of the nucleic acid sequence set forth in SEQ ID NO:1 under conditions of 5×SSC at 65° C. for 16 hours followed by one wash in 1.0×SSC at 55° C. for 30 minutes.

2. An isolated nucleic acid molecule of claim 1 encoding an angiosperm geranyl diphosphate synthase large subunit protein.

3. An isolated nucleic acid molecule of claim 1 encoding a gymnosperm geranyl diphosphate synthase large subunit protein.

4. An isolated nucleic acid molecule of claim 1 encoding an essential oil plant geranyl diphosphate synthase large subunit protein.

5. An isolated nucleic acid molecule of claim 1 encoding a Lamiaceae geranyl diphosphate synthase large subunit protein.

6. An isolated nucleic acid molecule of claim 1 encoding a Mentha geranyl diphosphate synthase large subunit protein.

7. An isolated nucleic acid molecule of claim 6 encoding a *Mentha piperita* geranyl diphosphate synthase large subunit protein.

8. An isolated nucleic acid molecule of claim 7 comprising the nucleotide sequence set forth in SEQ ID NO:1.

9. An isolated nucleic acid molecule of claim 1 encoding a geranyl diphosphate synthase large subunit protein comprising the amino acid sequence of SEQ ID NO:2.

10. A replicable expression vector comprising a nucleic acid molecule of claim 1.

11. A replicable expression vector of claim 10 comprising a nucleic acid molecule encoding a Lamiaceae geranyl diphosphate synthase large subunit protein.

12. A replicable expression vector of claim 10 comprising a nucleic acid molecule encoding a Mentha geranyl diphosphate synthase large subunit protein.

13. A host cell comprising a vector of claim 10.

14. A host cell comprising a vector of claim 11.

15. A host cell comprising a vector of claim 12.

16. A method of imparting or enhancing the production of geranyl diphosphate synthase large subunit in a host cell comprising introducing into the host cell an expression vector comprising a nucleic acid molecule encoding a geranyl diphosphate synthase large subunit protein under conditions enabling expression of the large subunit protein in the host cell, wherein said nucleic acid molecule encoding a geranyl diphosphate synthase large subunit protein hybridizes to the complement of a nucleic acid molecule consisting of the nucleic acid sequence set forth in SEQ ID NO:1 under conditions of 5×SSC at 65° C. for 16 hours followed by one wash in 1.0×SSC at 55° C. for 30 minutes.

17. The method of claim 16 wherein the host cell is a eukaryotic cell.

18. The method of claim 17 wherein the host cell is a plant cell.

19. The method of claim 17 wherein the host cell is an animal cell.

20. A method of imparting or enhancing the production of geranyl diphosphate synthase in a host cell comprising introducing into the host cell an expression vector comprising a nucleic acid molecule encoding a geranyl diphosphate synthase large subunit protein and a nucleic acid molecule encoding a geranyl diphosphate synthase small subunit protein under conditions enabling expression of the large and small subunit proteins in the host cell, wherein:
   (1) said nucleic acid molecule encoding a geranyl diphosphate synthase large subunit protein hybridizes to the complement of a nucleic acid molecule consisting of the nucleic acid sequence set forth in SEQ ID NO:1 under conditions of 5×SSC at 65° C. for 16 hours followed by one wash in 1.0×SSC at 55° C. for 30 minutes; and
   (2) said nucleic acid molecule encoding a geranyl diphosphate synthase small subunit hybridizes to the complement of a nucleic acid molecule consisting of the nucleic acid sequence set forth in SEQ ID NO:10 under conditions of 5×SSC at 65° C. for 16 hours followed by one wash in 1.0×SSC at 55° C. for 30 minutes.

21. The method of claim 20 wherein the host cell is a eukaryotic cell.

22. The method of claim 21 wherein the host cell is a plant cell.

23. The method of claim 22 wherein the host cell is an animal cell.

24. An isolated nucleic acid molecule that hybridizes to a nucleic acid molecule consisting of the nucleic acid sequence set forth in SEQ ID NO:1, or to a nucleic acid molecule consisting of the complement of a nucleic acid molecule consisting of the nucleic acid sequence set forth in SEQ ID NO:1, under stringent conditions of 5×SSC at 65° C. for 16 hours followed by one wash in 1.0×SSC at 55° C. for 30 minutes.

\* \* \* \* \*